United States Patent
Backer et al.

(10) Patent No.: US 9,518,072 B2
(45) Date of Patent: *Dec. 13, 2016

(54) ESTER-FUNCTIONAL SILANES AND THE PREPARATION AND USE THEREOF; AND USE OF IMINIUM COMPOUNDS AS PHASE TRANSFER CATALYSTS

(71) Applicant: Dow Corning Corporation, Midland, MI (US)

(72) Inventors: Michael Wolfgang Backer, Mainz (DE); John Michael Gohndrone, Midland, MI (US); Don Lee Kleyer, Hemlock, MI (US); Xiaobing Zhou, Midland, MI (US)

(73) Assignee: Dow Corning Corporation, Midland, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/361,790

(22) PCT Filed: Nov. 14, 2012

(86) PCT No.: PCT/US2012/064905
§ 371 (c)(1),
(2) Date: May 30, 2014

(87) PCT Pub. No.: WO2013/081820
PCT Pub. Date: Jun. 6, 2013

(65) Prior Publication Data
US 2015/0126676 A1    May 7, 2015

Related U.S. Application Data

(60) Provisional application No. 61/566,277, filed on Dec. 2, 2011.

(51) Int. Cl.
| | | |
|---|---|---|
| C07F 7/18 | (2006.01) | |
| B60C 1/00 | (2006.01) | |
| C08K 5/5419 | (2006.01) | |
| C08K 5/5425 | (2006.01) | |
| C07F 7/08 | (2006.01) | |

(52) U.S. Cl.
CPC ............ *C07F 7/1892* (2013.01); *B60C 1/00* (2013.01); *B60C 1/0016* (2013.04); *C07F 7/1836* (2013.01); *C08K 5/5419* (2013.01); *C08K 5/5425* (2013.01); *C07F 7/0818* (2013.01); *C07F 7/1876* (2013.01)

(58) Field of Classification Search
CPC ...... C07F 7/1892; C07F 7/1876; C07F 7/0818
See application file for complete search history.

(56) References Cited

U.S. PATENT DOCUMENTS

| | | |
|---|---|---|
| 3,179,612 A | 4/1965 | Plueddermann |
| 3,307,967 A | 3/1967 | Vanderbilt et al. |
| 3,443,620 A | 5/1969 | Vanderbilt et al. |
| 3,769,244 A | 10/1973 | Hashimoto et al. |
| 4,281,145 A | 7/1981 | Mitchell |
| 4,379,766 A | 4/1983 | Mack et al. |
| 4,465,867 A | 8/1984 | Maekawa et al. |
| 4,465,868 A | 8/1984 | Maekawa et al. |
| 4,496,682 A | 1/1985 | Schmiegel |
| 4,524,104 A | 6/1985 | Hagio et al. |
| 4,845,259 A | 7/1989 | Arai et al. |
| 4,910,260 A | 3/1990 | Wachi et al. |
| 4,946,977 A | 8/1990 | Bernhardt et al. |
| 5,041,593 A | 8/1991 | Plueddemann |
| 5,082,968 A | 1/1992 | Brunelle |
| 5,089,300 A | 2/1992 | Plueddemann |
| 5,117,027 A | 5/1992 | Bernhardt et al. |
| 5,229,482 A * | 7/1993 | Brunelle ............ C08G 65/4087 528/125 |
| 5,274,184 A | 12/1993 | Nagl et al. |
| 5,371,216 A | 12/1994 | Bernhardt et al. |
| 5,409,998 A | 4/1995 | Chiodini et al. |
| 5,451,625 A | 9/1995 | Fukushi |
| 5,658,671 A | 8/1997 | Fukushi |
| 5,679,821 A | 10/1997 | Takei et al. |
| 5,684,065 A | 11/1997 | Hiraoka et al. |
| 5,712,407 A | 1/1998 | Kreutzberger et al. |
| 5,750,753 A | 5/1998 | Kimae et al. |
| 5,811,479 A | 9/1998 | Labauze |
| 5,870,275 A | 2/1999 | Shiono et al. |
| 5,905,150 A | 5/1999 | Simonian et al. |
| 5,959,037 A | 9/1999 | Saito et al. |
| 6,071,995 A | 6/2000 | Labauze |

(Continued)

FOREIGN PATENT DOCUMENTS

| | | |
|---|---|---|
| DE | 102010063082 | 6/2011 |
| JP | 56104890 | 8/1981 |

(Continued)

OTHER PUBLICATIONS

Arbin, Astrid, et. al., "Alkylation of carboxylic acids by solid-liquid phase-transfer catalysis for determination by gas chromatography", Journal of Chromatography A., vol. 170, Issue 1, Feb. 11, 1979.

(Continued)

*Primary Examiner* — Margaret Moore
(74) *Attorney, Agent, or Firm* — Matthew T. Fewkes

(57) ABSTRACT

A method for producing a reaction product comprising an ester-functional silane, the method comprising: i) reacting a composition comprising: a) a haloorganosilane, b) a metal salt of a carboxy-functional compound, c) a phase transfer catalyst comprising a bicyclic amidine, an iminium compound, or a mixture thereof, provided that the iminium compound is not an acyclic guanidinium compound or pyridinium compound, and d) a co-catalyst, provided that the co-catalyst is optional when the phase transfer catalyst comprises the iminium compound.

11 Claims, No Drawings

(56) References Cited

U.S. PATENT DOCUMENTS

| | | | |
|---|---|---|---|
| 6,114,473 | A | 9/2000 | Miyake et al. |
| 6,262,879 | B1 | 7/2001 | Nitta et al. |
| 6,329,471 | B1 | 12/2001 | Mizuide et al. |
| 6,448,427 | B1 | 9/2002 | Wakita et al. |
| 6,608,225 | B1 | 8/2003 | Larson et al. |
| 6,815,554 | B2 | 11/2004 | Pfeiffer et al. |
| 6,900,263 | B2 | 5/2005 | Hodge |
| 6,903,155 | B2 | 6/2005 | Hodge |
| 7,078,449 | B2 | 7/2006 | Pagano et al. |
| 7,186,776 | B2 | 3/2007 | Tardivat et al. |
| 7,256,233 | B2 | 8/2007 | Simonot et al. |
| 7,262,312 | B2 | 8/2007 | Sheridan et al. |
| 7,271,228 | B2 | 9/2007 | Armand et al. |
| 7,300,970 | B2 | 11/2007 | Durel et al. |
| 7,528,273 | B2 | 5/2009 | Simandan et al. |
| 7,629,408 | B2 | 12/2009 | Cambon et al. |
| 7,718,717 | B2 | 5/2010 | Lapra et al. |
| 7,758,897 | B2 | 7/2010 | Roettger et al. |
| 7,851,627 | B2 | 12/2010 | Mezei et al. |
| 7,858,802 | B2 | 12/2010 | Maase et al. |
| 7,956,225 | B2 | 6/2011 | Sato et al. |
| 8,044,120 | B2 | 10/2011 | D'Andola et al. |
| 8,404,139 | B2 | 3/2013 | Dubois et al. |
| 8,404,140 | B2 | 3/2013 | Dubois et al. |
| 8,569,417 | B2 | 10/2013 | Backer et al. |
| 8,580,886 | B2 * | 11/2013 | Backer .............. C07F 7/1836 524/576 |
| 8,618,225 | B2 | 12/2013 | Toufaili |
| 2003/0163000 | A1 | 8/2003 | Atkinson et al. |
| 2009/0235574 | A1 | 9/2009 | Earle et al. |
| 2010/0310853 | A1 | 12/2010 | Schwiegk et al. |
| 2012/0004437 | A1 | 1/2012 | Stanjek et al. |
| 2012/0007020 | A1 | 1/2012 | Tarascon et al. |
| 2012/0059121 | A1 | 3/2012 | Backer et al. |
| 2012/0065319 | A1 | 3/2012 | Backer et al. |
| 2013/0060057 | A1 * | 3/2013 | Daiss ................ C07F 7/1892 556/440 |

FOREIGN PATENT DOCUMENTS

| | | |
|---|---|---|
| JP | 63268757 | 11/1988 |
| JP | 05306290 | 11/1993 |
| JP | 06345784 | 12/1994 |
| JP | 09124760 | 5/1997 |
| JP | 09137149 | 5/1997 |
| JP | 09157623 | 6/1997 |
| JP | 1998017798 | 1/1998 |
| JP | 1105375 | 2/1999 |
| JP | 11050033 | 2/1999 |
| JP | 11054376 | 2/1999 |
| JP | 11054377 | 2/1999 |
| JP | 11054379 | 2/1999 |
| JP | 11238653 | 8/1999 |
| JP | 2000232037 | 8/2000 |
| JP | 2002321981 | 11/2002 |
| JP | 2002334815 | 11/2002 |
| JP | 2003272956 | 9/2003 |
| JP | 2003301143 | 10/2003 |
| JP | 2003324039 | 11/2003 |
| JP | 2005197665 | 7/2005 |
| JP | 2006104143 | 4/2006 |
| JP | 2006089379 | 6/2006 |
| JP | 2006156728 | 6/2006 |
| JP | 2006206440 | 8/2006 |
| JP | 2007039653 | 2/2007 |
| JP | 2008202023 | 9/2008 |
| JP | 2008266556 | 11/2008 |
| JP | 2008266557 | 11/2008 |
| JP | 2009007565 | 1/2009 |
| JP | 2010070539 | 4/2010 |
| JP | 2010138234 | 6/2010 |
| JP | 2010150461 | 7/2010 |
| JP | 2011148711 | 8/2011 |
| PL | 182004 | 12/1996 |
| WO | 2005/103061 | * 11/2005 |
| WO | 2005103061 | 11/2005 |
| WO | 2006111712 | 10/2006 |
| WO | 2007118923 | 10/2007 |
| WO | 2010000834 | 1/2010 |
| WO | 2010116594 | 10/2010 |

OTHER PUBLICATIONS

Aziz, et. al. "Cation-Specific Interactions with Carboxylate in Amino Acid and Acetate Aqueous Solutions: X-ray Absorption and ab initio Calculations", Journal of Physical Chemistry B Letters, 2008, 12567-12570, 112.

Baidya, Mahiuddin, "Nucleophilicites and Lewis Basicities of Tertiary Amines: A Key to Rationalize Nucleophilic Organocatalysis", Ludwig-Maximillians University, Thesis, 2009, Karalirchack, India.

Blanco, Carlos, et. al., "Alkylation of naphthalene using three different ionic liquids", Journal of Molecular Catalysis, Apr. 24, 2006, pp. 203-206.

Chen, Xinzhi, et. al. "DBU Derived Ionic Liquids and Their Application in Organic Synthetic Reactions", School of Pharmaceutical and Chemical Engineering, 305-330, 14, Taizhou University, Taizhou, P.R. China.

Coles, Martyn P., "Bicyclic-guanidines, -guanidinates and -guanidinium salts: wide ranging applications from a simple family of molecules", 2009, pp. 3659-3676, The Royal Society of Chemistry.

Cotton, F. Albert et. al. "Homologus of the Easily Ionized Compound Mo2(hpp)4 Containing Smaller Cicyclic Guanidinates", Inorg. Chem. 2006, 45, pp. 5493-5500.

Dehmlow, E.V., "Tetramethylammonium Salts as Phase Transfer Catalysts", SACHEM Inc., 2008.

Fedorynski, Michal, et. al. "Phase transfer catalyzed (PTC) reactions of chloroform with alkenyl carboxylates. Effect of catalyst structure on reaction course", Tetrahedron, vol. 53, Issue 3, Jan. 20, 1997.

Ghobril, Cynthia, et. al. "Structure-Reactivity Relationship Studies for Guanidine-Organocatalyzed Direct Intramolecular Aldolization of Ketoaldehydes", ChemCatChem, 2010, 2, 1573-1581, Wiley-VCH.

Hajipour, et. al. "Basic Ionic Liquids. A Short Review", J. Iran. Chem. Soc., Dec. 4, 2009, pp. 647-678, vol. 6, No. 4.

Im, Yang., et. al. "Nucleophilic Behaviour of DBU and DBN toward Acetylated Baylis-Hillman Adducts", Bull. Korean Chem. Soc., 2001, 1053-1055, vol. 22, No. 9, Chonnam National Univeristy, Kwangju, Korea.

Kiesewetter, Matthew K., "Cyclic Guanidine Organic Catalysts: What is Magic About Triazabicyclodecene?", J. Org. Chem., 2009, pp. 9490-9496, 74. Supporting documentation included.

Kuo, et. al., "Inverse Phase Transfer Catalysis. Kinetics and Mechanism of the Pyridine 1-Oxide-Catalyzed Substitution Reaction of Benzoyl Chloride and Benzoate Ion in a Two-Phase WaterIDichloromethan Medium", J. Org. Chem., 1992, 1991-1995, vol. 57, National Cheng Kung University, Tainan, Taiwan.

Lecuyer, Julien, "Organocatalytic decomposition of poly(ethylene terephthalate) using triazabicyclodecene proposal", Master's Theses and Graduate Research, 2010, San Jose State University.

Makosza, Mieczyslaw, et. al. "Co-catalysis in phase transfer catalyzed reactions (a concept paper)", Arkivoc 2006 (iv), 7-17, Inst. of Organic Chemistry, Polish Academy of Sciences, Kasprzaka, Warszawa.

Sirovskii, F.S., et. al. "Inhibition and synergism in phase transfer catalysis" Russian Chemical Reviews, 1991, 60 (4), pp. 345-357.

Sobral, et. al., "Synthesis and crystal structure of new phase-transfer catalysts based on 1,8-diazabicyclo[5.4.0] undec-7-ene and 1,5-diazabicyclo[4.3.0]non-5-ene", Progr. Colloid Polym. Sci, 2004, 28-30, 123, Springer-Verlag.

Starks, Charles M., et. al. "Variables in Reaction Design for Laboratory and Industrial Applications of Phase-Transfer Catalysis", Phase-Transfer Catalysis Fundamentals, Applications, and Industrial Perspectives (book), pp. 266-338, Chapman & Hall, 1994.

(56) References Cited

OTHER PUBLICATIONS

Vlachy, et. al., "Hofmeister series and specific interactions of charged headgroups with aqueous ions", Advances in Colloid and Interface Science, 2008, 1-6, Regensburg, Germany.
Ying, et. al., "Green and efficient aza-Michael additions of aromatic amines to a,b-unsaturdated ketones catalyzed by DBU based task-specific ionic liquids without solvent", Arkat USA, Inc., 288-298.

* cited by examiner

ESTER-FUNCTIONAL SILANES AND THE PREPARATION AND USE THEREOF; AND USE OF IMINIUM COMPOUNDS AS PHASE TRANSFER CATALYSTS

CROSS REFERENCE TO RELATED APPLICATIONS

This application is a U.S. national stage filing under 35 U.S.C. §371 of PCT Application No. PCT/US12/64905 filed on 14 Nov. 2012, currently pending, which claims the benefit of U.S. Provisional Patent Application No. 61/566, 277 filed 2 Dec. 2011 under 35 U.S.C. §119 (e). PCT Application No. PCT/US12/64905 and U.S. Provisional Patent Application No. 61/566,277 are hereby incorporated by reference.

The present invention relates to new ester-functional silanes, a new method of synthesizing and using ester-functional silanes, and a new use of iminium compounds as phase transfer catalysts. The ester-functional silanes are useful in tire formulations or as adhesion promoters. The new synthetic route may produce the ester-functional silanes faster, at a lower temperature, and/or with fewer by-products than conventional methods for producing ester-functional silanes.

Phase transfer catalyzed reaction of a metal carboxylate with a haloorganosilane can be performed using a quaternary ammonium catalyst, such as benzyltrimethylammonium chloride. However, benzyltrimethylammonium chloride suffers from the drawback of being thermally unstable at temperatures used for this reaction, and thus would not be considered a high performance catalyst. Tetrabutylammonium halides, such as tetrabutylammonium bromide (TBAB), may also be thermally unstable at the temperatures needed to produce the ester functional silanes. Using TBAB as a phase transfer catalyst may result in catalyst decomposition products, e.g., tributylamine and butylcarboxylates, being present in the product.

Amine quat salts suffer from being less thermally stable and less efficient (since they are decomposing under the conditions of the reaction) and can generate undesired by-products during the reaction and afterwards during recovery of the product, e.g., by elevated temperature distillation of the product away from the catalyst residue than phosphonium compounds. The decomposition by-products can be difficult to separate by distillation because of similarity of boiling point and because they are being continually generated during attempts at purification.

Phase transfer catalyzed reaction of a metal carboxylate with a haloorganosilane with use of phosphonium salts such as $Ph_3PMeCl$ suffer from the drawback that phosphonium compounds are more toxic than their ammonium counterparts.

A thermally-stable, amine-based phase transfer catalyst, hexaethylguanidinium chloride has also been disclosed. However, hexaethylguanidinium chloride is available as an aqueous solution that must be thoroughly dried before use, which is an undesirable additional, and energy consuming, process step. hexaethylguanidinium chloride also suffers from the drawback of being difficult to obtain in commercial quantities.

There is a continuing need in the art to provide alternative phase transfer catalysts. Phase transfer catalysts suitable for use in nonaqueous environments are desired.

BRIEF SUMMARY OF THE INVENTION

The present invention is directed to a method for producing a reaction product comprising an ester-functional silane comprising: i) reacting a composition comprising: a) a haloorganosilane, b) a metal salt of a carboxy-functional compound, c) a phase transfer catalyst comprising a bicyclic amidine, an iminium compound, or a mixture thereof, provided that the iminium compound is not an acyclic guanidinium compound or pyridinium compound, and d) a co-catalyst, provided that the co-catalyst is optional when the phase transfer catalyst comprises the iminium compound.

The invention is also directed to the ester-functional silane prepared by the method described above where the ester-functional silane has formula (V):

$$Y_a SiQ_{(4-a)}, \quad (V)$$

where
a is 1 or 2; each Q is independently $R^1$ or $OR^1$, wherein each $R^1$ is hydrocarbyl; Y is $R^{11}{}_2C\!=\!CH(CH_2)_d COOR^{10}\!-\!$, wherein d is an integer from 0 to 18; each $R^{11}$ is independently H, a hydrocarbyl group, or $-(CH_2)_d COOR^{10} SiQ_3$, wherein d is as defined above; and $R^{10}$ is a hydrocarbylene group having from 1 to 10 carbon atoms.

The invention is further directed to a rubber composition comprising: A) a diene polymer, B) a reinforcing filler, and C) the ester-functional silane described above.

The invention is still further directed to a method of preparing a reaction product, the method comprising combing an iminium compound with a reaction medium comprising at least two phases, wherein the iminium compound acts as a phase transfer catalyst in the reaction medium and the iminium compound is not an acyclic guanidinium compound (define that acyclic means where guanidinium functionality is not part of the ring.) or pyridinium compound.

DETAILED DESCRIPTION OF THE INVENTION

All amounts, ratios, and percentages are by weight unless otherwise indicated. The articles 'a', 'an', and 'the' each refer to one or more, unless otherwise indicated by the context of specification. The disclosure of ranges includes the range itself and also anything subsumed therein, as well as endpoints. For example, disclosure of a range of 2.0 to 4.0 includes not only the range of 2.0 to 4.0, but also 2.1, 2.3, 3.4, 3.5, and 4.0 individually, as well as any other number subsumed in the range. Furthermore, disclosure of a range of, for example, 2.0 to 4.0 includes the subsets of, for example, 2.1 to 3.5, 2.3 to 3.4, 2.6 to 3.7, and 3.8 to 4.0, as well as any other subset subsumed in the range. Similarly, the disclosure of Markush groups includes the entire group and also any individual members and subgroups subsumed therein. For example, disclosure of the Markush group a hydrogen atom, an alkyl group, an aryl group, an aralkyl group, or an alkaryl group includes the member alkyl individually; the subgroup alkyl and aryl; and any other individual member and subgroup subsumed therein.

"Quat" and "iminium" are used interchangeably to describe salts with a nitrogen-carbon double-bond and the structure $R_2C\!=\!N^+R_2Y^-$, where R is hydrogen or hydrocarbyl and $Y^-$ is an anion such as a halide.

"Aralkyl" and "alkaryl" each refer to an alkyl group having a pendant and/or terminal aryl group or an aryl group having a pendant alkyl group. Exemplary aralkyl groups include benzyl, phenylethyl, phenyl propyl, and phenyl butyl.

"Cycloalkyl" refers to a saturated carbocycle. Cycloalkyl groups are exemplified by cyclobutyl, cyclopentyl, and cyclohexyl.

"Heterocycle" and "heterocyclic" refer to a ring group comprised of carbon atoms and one or more heteroatoms in the ring. The heteroatom may be N, O, P, S, or a combination thereof. Alternatively, the heteroatom may be N. Heterocycles may be monocyclic or alternatively may be fused, bridged, or spiro polycyclic rings. Monocyclic heterocycles may have 3 to 9 member atoms in the ring, alternatively 4 to 7 member atoms, and alternatively 5 to 6 member atoms. Polycyclic heterocycles may have 7 to 17 member atoms, alternatively 7 to 14 member atoms, and alternatively 9 to 11 member atoms. Heterocycles may be saturated or partially unsaturated.

"Poly", as used herein as a prefix, is intended to mean more than one.

Abbreviations used herein are defined as follows. "GC" means gas chromatography. "NMR" means nuclear magnetic resonance. The abbreviation "ppm" means parts per million. "Et" means ethyl. "Me" means methyl. "Ph" means phenyl. "Pr" means propyl and includes various structures such as iPr and nPr. "iPr" means isopropyl. "nPr" means normal propyl. "Bu" means butyl and includes various structures including nBu, sec-butyl, tBu, and iBu. "iBu" means isobutyl. "nBu" means normal butyl. "tBu" means tertiary-butyl. "Vi" means vinyl.

A method for producing a reaction product comprising an ester-functional silane, the method comprising: i) reacting a composition comprising:

a) a haloorganosilane, b) a metal salt of a carboxy-functional compound, c) a phase transfer catalyst comprising a bicyclic amidine, an iminium compound, or a mixture thereof, provided that the iminium compound is not an acyclic guanidinium compound or pyridinium compound, and d) a co-catalyst, provided that the co-catalyst is optional when the phase transfer catalyst comprises the iminium compound.

The haloorganosilane may have formula (I): $X_a SiQ_{(4-a)}$ (I), where subscript a is 1 or 2, alternatively 1; Q is $R^1$ or $OR^1$, wherein $R^1$ is hydrocarbyl; each X is independently a halogenated organic group. X may be an alkyl group which contains at least one halogen atom such as Cl, Br, or I; alternatively Cl. Exemplary groups for X include chloromethyl, chloropropyl, bromopropyl, iodopropyl, or chloroisobutyl. Alternatively, X may be selected from chloromethyl and chloropropyl.

In formula (I), each Q is independently $R^1$ or $OR^1$, wherein each $R^1$ is independently hydrocarbyl. The hydrocarbyl groups represented by $R^1$ typically have 1 to 10 carbon atoms, alternatively 1 to 4 carbon atoms. Acyclic hydrocarbyl groups containing at least three carbon atoms can have a branched or unbranched structure. Examples of hydrocarbyl groups for $R^1$ include, but are not limited to, alkyl, such as Me, Et, Pr, 1-methylethyl, Bu, 1-methylpropyl, 2-methylpropyl, 1,1-dimethylethyl, pentyl, 1-methylbutyl, 1-ethylpropyl, 2-methylbutyl, 3-methylbutyl, 1,2-dimethylpropyl, 2,2-dimethylpropyl, hexyl; cycloalkyl, such as cyclopentyl, cyclohexyl, and butylcyclohexyl; aryl, such as phenyl; alkenyl, such as vinyl, allyl, and propenyl; and alkynyl, such as ethynyl and propynyl.

Examples of the haloorganosilane of formula (I) include, but are not limited to, chloromethyldimethylmethoxysilane, chloromethyltrimethoxysilane, chloromethyltriethoxysilane, 3-chloropropyltrimethoxysilane, 3-chloropropyltriethoxysilane, 3-chloropropylmethyldimethoxysilane, 3-chloropropylmethyldiethoxysilane, 3-chloropropyldimethylmethoxysilane, 3-chloropropyldimethylethoxysilane, 3-chloropropylethyldimethoxysilane, 3-chloropropylethyl-diethoxysilane, 3-bromopropyltrimethoxysilane, 3-bromopropyltriethoxysilane, 3-iodopropyltrimethoxysilane, 3-iodopropyltriethoxysilane, chlorobutylphenylmethyl-n-propoxysilane, chloromethyldimethylmethoxysilane, or chloromethyltrimethoxysilane. Alternatively, the haloorganosilane of formula (I) is 3-chloropropyltrimethoxysilane or 3-chloropropyltriethoxysilane.

The amount of haloorganosilane for ingredient a) may range from 1% to 99%, based on the combined weights of ingredients a) and b). Alternatively, the amounts of ingredient a) and ingredient b) may be selected to provide a 2:1 molar ratio of haloorganosilane and metal salt of a carboxylic acid; alternatively a molar ratio of 1:1. One skilled in the art would understand that the molar ratio would be chosen based on the number of carboxylate groups in the metal salt of the carboxy-functional compound.

The metal salt of a carboxy-functional compound has the formula $[R^2COO^-]_c[M^{c+}]$ (II), wherein $R^2$ is substituted or unsubstituted hydrocarbyl, each $M^{c+}$ is an alkali metal cation, alkaline earth metal cation, or ammonium cation and c is 1 or 2. Examples of alkali metal, alkaline earth metal, ammonium cations represented by $M^{c+}$ include $Li^+$, $Na^+$, $K^+$, $Mg^{2+}$, $Ca^{2+}$, tetramethylammonium, tetraethylammonium, trimethylammonium, and triethylammonium. In one embodiment, $M^{c+}$ is $Na^+$ or $K^+$.

The hydrocarbyl groups represented by $R^2$ typically have from 1 to 20 carbon atoms, alternatively from 1 to 12 carbon atoms, alternatively from 1 to 3 carbon atoms. Acyclic hydrocarbyl groups containing at least three carbon atoms can have a branched or unbranched structure. Examples of hydrocarbyl groups include, but are not limited to, alkyl, such as methyl, ethyl, propyl, 1-methylethyl, butyl, 1-methylpropyl, 2-methylpropyl, 1,1-dimethylethyl, pentyl, 1-methylbutyl, 1-ethylpropyl, 2-methylbutyl, 3-methylbutyl, 1,2-dimethylpropyl, 2,2-dimethylpropyl, hexyl, heptyl, octyl, nonyl, decyl, dodecyl, and octadecyl; cycloalkyl, such as cyclopentyl and cyclohexyl; aryl, such as phenyl and naphthyl; arylalkyl, such as benzyl; alkenyl, such as vinyl, allyl, propenyl, butenyl, pentenyl, hexenyl, heptenyl, octenyl, nonenyl, and decenyl; and alkynyl, such as ethynyl, propynyl, butynyl, pentynyl, hexynyl, heptynyl, octynyl, nonynyl, decynyl, and dodecynyl.

$R^2$ may be substituted. Examples of substitute groups for $R^2$ include, but are not limited to, F, $[—COO^-]_c[M^{c+}]$, OH, $OR^1$, $OCH_2CH_2OR^1$, $COOR^1$, $C(=O)NR^1$, or $C(=O)NH$, $C(=O)NR^1_2$, $C(=O)NH_2$ where $M^{c+}$, $R^1$, and c are as defined above. Alternatively, $R^2$ is substituted with $[—COO^-]_c[M^{c+}]$, where $M^{c+}$ and c are as defined above.

Examples of the metal salt of a carboxy-functional compound include, but are not limited to, sodium acrylate, sodium methacrylate, sodium ethacrylate (i.e., sodium 2-methylenebutanoate), sodium crotonate, sodium isocrotonate, sodium sorbate, potassium acrylate, potassium methacrylate, potassium ethacrylate (i.e., potassium 2-methylenebutanoate), potassium crotonate, potassium isocrotonate, potassium sorbate, magnesium acrylate, magnesium methacrylate, magnesium ethacrylate, magnesium crotonate, magnesium isocrotonate, magnesium sorbate, calcium acrylate, calcium methacrylate, calcium ethacrylate, calcium crotonate, calcium isocrotonate, and calcium sorbate, monosodium fumarate, disodium fumarate, monosodium maleate, disodium maleate, monosodium itaconate, disodium itaconate, monopotassium fumarate, dipotassium fumarate, monopotassium maleate, dipotassium maleate, monopotassium itaconate, dipotassium itaconate, sodium 10-undecenoate, and potassium 10-undecenoate, sodium, arachidate, sodium stearate, sodium palmitate, sodium erucate, sodium oleate, sodium linolenate, and sodium arachidonate.

Processes of preparing metal salts of carboxy-functional compounds are well known in the art, and many of these compounds are commercially available. For example, the metal salt of an unsaturated carboxylic acid may be prepared by adding an unsaturated carboxylic acid dropwise to a solution of NaOEt in ethanol while, for example, maintaining the temperature below 25° C. while stirring.

The phase transfer catalyst of ingredient c) comprises a bicyclic amidine, an iminium compound, or a mixture thereof, provided that the iminium compound is not an acyclic guanidinium compound or pyridinium compound. As used herein, "acyclic guanidinium" is intended to mean compounds that may or may not have ring structures as part of the guanidinium compound but, if the guanidinium compound does have a ring structure, the guanidinium functionality does not form part of the ring. Ingredient c) may comprise a polyazapolycycloalkene, such as a polyazabicycloalkene. Alternatively, ingredient c) may comprise a polyazapolycycloalkenium, such as a polyazabicycloalkenium. Suitable polyazabicycloalkenes, and salts thereof; and methods for their preparation are disclosed, for example, in U.S. Pat. Nos. 3,769,244; 4,524,104; 4,465,867; and 4,465,868. Alternatively, the phase transfer catalyst of ingredient c) may comprise a diazabicycloalkene such as those disclosed in U.S. Pat. Nos. 3,769,244 and 4,524,104 at col. 2, at lines 31-54. Examples of diazabicycloalkenes include, but are not limited to, i) 1,5-diazabicyclo[4.2.0]oct-5-ene; ii) 1,8-diazabicyclo[7.2.0]undec-8-ene; iii) 1,4-diazabicyclo[3.3.0]oct-4-ene; iv) 3-methyl-1,4-diazabicyclo[3.3.0]oct-4-ene; v) 3,6,7,7-tetramethyl-1,4-diazabicyclo[3.3.0]oct-4-ene; vi) 7,8,8-trimethyl-1,5-diazabicyclo[4.3.0]non-5-ene; vii) 1,8-diazabicyclo[7.3.0]tridec-8-ene; viii) 1,7-diazabicyclo[4.3.0]non-6-ene; ix) 1,5-diazabicyclo[4.4.0]dec-5-ene; x) 1,5-diazabicyclo[4.3.0]non-5-ene (DBN); xi) 1,8-diazabicyclo[7.4.0]tridec-8-ene; xii) 1,8-diazabicyclo[7.3.0]dodec-8-ene; xiii) 1,8-diazabicyclo[5.3.0]dec-7-ene; xiv) 9-methyl-1,8-diazabicyclo[5.3.0]dec-7-ene; xv) 9-methyl-1,8-diazabicyclo[5.4.0]undec-7-ene; xvi) 1,8-diazabicyclo[5.4.0]undec-7-ene (DBU); xvii) 1,6-diazabicyclo[5.5.0]dodec-6-ene; xviii) 1,7-diazabicyclo[6.5.0]tridec-7-ene; xix) 1,8-diazabicyclo[7.5.0]tetradec-8-ene; xx) 1,10-diazabicyclo[7.3.0]dodec-9-ene; xxi) 1,10-diazabicyclo[7.4.0]tridec-9-ene; xxii) 1,14-diazabicyclo[11.3.0]hexadec-13-ene; xxiii) 1,14-diazabicyclo[11.4.0]heptadec-13-ene; xxiv) 1,8-diazabicyclo[5.3.0]dec-7-ene; and xxv) combinations thereof.

Alternatively, the polyazapolycycloalkene may comprise a triazabicycloalkene, such as 1,5,7-triazabicyclo[4.4.0]dec-5-ene or 7-methyl-1,5,7-triazabicyclo[4.4.0]dec-5-ene (MTBD), both of which are commercially available from Sigma-Aldrich, Inc. of St. Louis, Mo., U.S.A.

Alternatively, the polyaza, polycycloalkene may be a polyazabicycloalkene selected from the group consisting of DBU, DBN, MTBD, or a combination thereof. Alternatively, the polyazabicycloalkene may be selected from the group consisting of DBN and MTBD, see structures below.

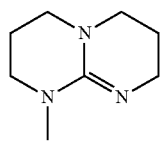
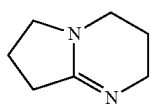

MTBD      DBN

The polyaza, polycycloalkene may have general formula (IV):

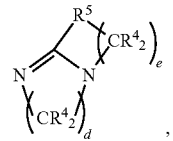

where
each $R^4$ is independently a hydrogen atom or a monovalent hydrocarbyl group,
$R^5$ is a divalent organic group, and
subscript d is an integer with a value of at least 2, and
subscript e is an integer with a value of at least 1.

The hydrocarbyl groups represented by $R^4$ may have 1 to 18 carbon atoms, alternatively 1 to 12 carbon atoms, alternatively 1 to 6 carbon atoms, and alternatively 1 to 4 carbon atoms. Acyclic hydrocarbyl groups containing at least three carbon atoms can have a branched or unbranched structure. Examples of hydrocarbyl groups for $R^4$ include, but are not limited to, alkyl, such as Me, Et, Pr, 1-methylethyl, Bu, 1-methylpropyl, 2-methylpropyl, 1,1-dimethylethyl, pentyl, 1-methylbutyl, 1-ethylpropyl, 2-methylbutyl, 3-methylbutyl, 1,2-dimethylpropyl, 2,2-dimethylpropyl, hexyl; cycloalkyl, such as cyclopentyl and cyclohexyl; aryl, such as phenyl; alkenyl, such as vinyl, allyl, and propenyl; and alkynyl, such as ethynyl and propynyl. Alternatively, each $R^4$ may be a hydrogen atom or an alkyl group of 1 to 4 carbon atoms. Alternatively, each $R^4$ may be a hydrogen atom. In formula (IV), the divalent organic groups for $R^5$ may be alkylene groups such as $(CR^4_2)_d$, where $R^4$ and subscript d are as defined above. Alternatively, the divalent organic group for $R^5$ may contain a heteroatom. The divalent organic group for $R^5$ may have formula: $R^8N(CR^4_2)_d$ where $R^4$ and subscript d are as defined above and $R^8$ is a hydrogen atom or a hydrocarbyl group that may have 1 to 6 carbon atoms, alternatively 1 to 4 carbon atoms. Examples of hydrocarbyl groups for $R^8$ include, but are not limited to, alkyl, such as Me, Et, Pr, 1-methylethyl, Bu, 1-methylpropyl, 2-methylpropyl, 1,1-dimethylethyl, pentyl, 1-methylbutyl, 1-ethylpropyl, 2-methylbutyl, 3-methylbutyl, 1,2-dimethylpropyl, 2,2-dimethylpropyl, hexyl; cycloalkyl, such as cyclopentyl and cyclohexyl; aryl, such as phenyl; alkenyl, such as vinyl, allyl, and propenyl; and alkynyl, such as ethynyl and propynyl. Alternatively, each $R^8$ may be a hydrogen atom or Me. Alternatively in formula (IV), subscript d may be an integer with a value ranging from 2 to 6, alternatively 2 to 4. Alternatively, subscript d may be an integer with a value ranging from 2 to 6, alternatively 2 to 4.

The iminium compound may have general formula (IIa):

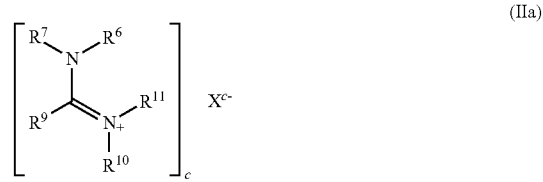

(IIa)

where c is 1 or 2 and $X^{c-}$ is counter ion selected from the group consisting of $Cl^-$, $Br^-$, $I^-$, $HSO_4^-$, $HCO_3^-$, acetate, $SO_4^{2-}$, $CO_3^{2-}$, $HPO_4^{2-}$ and $PO_4^{3-}$; alternatively $X^{c-}$ is $I^-$, $Cl^-$, or $Br^-$; alternatively $Cl^-$, alternatively $Br^-$; each $R^6$, $R^7$, $R^9$, $R^{10}$, and $R^{11}$ are independently a hydrogen, a substituted or unsubstituted hydrocarbyl group, or, with another group, forms a 4-10 member heterocyclic ring. Although the cation is depicted on the $N^2$ nitrogen in (IIa), one skilled in the art would recognize that the cation may be delocalized and represented by different resonance structures.

The hydrocarbyl groups represented by $R^6$, $R^7$, $R^9$, $R^{10}$, and $R^{11}$ typically have from 1 to 20 carbon atoms, alternatively from 1 to 10 carbon atoms, alternatively from 1 to 8 carbon atoms. Examples of hydrocarbyl groups include, but are not limited to, those described for $R^2$ above and having the appropriate number of carbon atoms.

$R^6$, $R^7$, $R^9$, $R^{10}$, and $R^{11}$ may be substituted with one or more of the same of different substitute groups, provided the substitutent does not prevent the functioning as a phase transfer catalyst. Examples of substitute groups include, but are not limited to, those described for $R^2$ above.

Alternatively $R^9$ and $R^7$, together with the nitrogen and carbon atoms to which they are bonded, form a 4- to 10-member ring comprising carbon and nitrogen, and, where the portion of the ring formed by $R^9$ and $R^7$ optionally comprises 1 or 2 nitrogen atoms and optionally has 1 or 2 $C_{1-8}$ hydrocarbyl groups pendant from the ring, and $R^{11}$ and $R^6$, together with the nitrogen atoms to which they are bonded and the carbon to which those nitrogen atoms are bonded, form a 5 to 10 member ring comprising carbon and nitrogen and, where the portion of the ring formed by $R^{11}$ and $R^6$ optionally comprises 1 or 2 nitrogen atoms and optionally has 1 or 2 $C_{1-8}$ hydrocarbyl groups pendant from the ring, and $R^{10}$ is $C_{6-10}$ alkyl.

Alternatively $R^9$ and $R^7$, together with the nitrogen and carbon atoms to which they are bonded, form a 4- to 7-member ring comprising carbon and nitrogen, and, where the portion of the ring formed by $R^9$ and $R^7$ optionally comprises one nitrogen, where the one nitrogen is bonded to the carbon atom that is between the two nitrogen atoms in (III) and has a pendant methyl group, and $R^{11}$ and $R^6$, together with the nitrogen atoms to which they are bonded and the carbon to which those nitrogen atoms are bonded, forms a 5 to 6 member ring comprising carbon and nitrogen and, where the portion of the ring formed by $R^{11}$ and $R^6$ optionally comprises no nitrogen atoms or pendant hydrocarbyl groups, and $R^{10}$ is $C_{6-10}$ alkyl.

Exemplary quaternary iminium compounds of bicyclic amidines suitable for ingredient c) include, but are not limited to, halides, acetates, sulfates, phosphates, and carbonates of compounds i) to xxiv) above. Alternatively, the quaternary iminium compound of the bicyclic amidine may be selected from the group consisting of:
i) 5-octyl-1,5-diazabicyclo-[4.2.0]oct-5-enium halide (e.g., bromide or chloride); ii) 8-undecyl-1,8-diazabicyclo-[7.2.0]undec-8-enium halide; iii) 4-octyl-1,4-diazabicyclo-[3.3.0]oct-4-enium halide; iv) 3-methyl-4-octyl-1,4-diazabicyclo[3.3.0]oct-4-enium halide; v) 3,6,7,7-tetramethyl-4-octyl-1,4-diazabicyclo[3.3.0]oct-4-enium halide; vi) 5-octyl-7,8,8-trimethyl-1,5-diazabicyclo[4.3.0]non-5-enium halide; vii) 8-tridecyl-1,8-diazabicyclo[7.3.0]dodec-8-enium halide; viii) 7-nonyl-1,7-diazabicyclo[4.3.0]non-6-enium halide; ix) 5-decyl-1,5-diazabicyclo[4.4.0]dec-5-enium halide; x) 5-nonyl-1,5-diazabicyclo[4.3.0]non-5-enium halide; xi) 8-tridecyl-1,8-diazabicyclo[7.4.0]tridec-8-enium halide; xii) 8-dodecyl-1,8-diazabicyclo[7.3.0]dodec-8-enium halide; xiii) 8-decyl-1,8-diazabicyclo[5.3.0]dec-7-enium halide; xiv) 8-decyl-9-methyl-1,8-diazabicyclo[5.3.0]dec-7-enim halide; xv) 8-undecyl-9-methyl-1,8-diazabicyclo[5.4.0]un-dec-7-enium halide; xvi) 8-undecyl-1,8-diazabicyclo[5.4.0]undec-7-enium halide; xvii) 6-octyl-1,6-diazabicyclo[5.5.0]dodec-6-enium halide; xviii) 7-tridecyl-1,7-diazabicyclo[6.5.0]tridec-7-enium halide; xix) 8-tetradecyl-1,8-diazabicyclo[7.5.0]tetradec-8-enium halide; xx) 10-dodecyl-1,10-diazabicyclo[7.3.0]dodec-9-enium halide; xxi) 10-tridecyl-1,10-diazabicyclo[7.4.0]tridec-9-enium halide; xxii) 14-hexadecyl-1,14-diazabicyclo[11.3.0]hexadec-13-enium halide; xxiii) 14-hapetadecyl-1,14-diazabicyclo[11.4.0]heptadec-13-enium halide; xxiv) 8-decyl-1,8-diazabicyclo[5.3.0]dec-7-enium halide; and xxv) combinations thereof.

Alternatively, the iminium compound of ingredient c) may be a $N^2$-alkyl-polyazapolycycloalkene halide compound selected from the group consisting of 8-octyl-1,8-diazabicyclo[5.4.0]-undec-7-enium bromide; 8-2-ethylhexyl-1,8-diazabicyclo[5.4.0]-undec-7-enium bromide; 5-octyl-1,5-diazabicyclo[4.3.0]non-5-enium bromide; 5-2-ethylhexyl-1,5-diazabicyclo[4.3.0]non-5-enium bromide; 4-octyl-1,4-diazabicyclo[2.2.2]octenium bromide; 4-2-ethylhexyl-1,4-diazabicyclo[2.2.2]octenium bromide; 5-octyl-7-methyl-1,5,7-triazabicyclo[4.4.0]dec-5-enium bromide; 5-2-ethylhexyl-7-methyl-1,5,7-triazabicyclo[4.4.0]dec-5-enium bromide; 8-butyl-1,8-diazabicyclo[5.4.0]-undec-7-enium bromide; 5-butyl-1,5-diazabicyclo[4.3.0]non-5-enium bromide; 4-butyl-1,4-diazabicyclo[2.2.2]octenium bromide; 7-butyl-7-methyl-1,5,7-triazabicyclo[4.4.0]dec-5-enium bromide or a combination thereof.

Alternatively, the iminium compound that is the phase transfer catalyst of ingredient c) may be selected from the group consisting of 8-octyl-1,8-diazabicyclo[5.4.0]-undec-7-enium bromide; 8-2-ethylhexyl-1,8-diazabicyclo[5.4.0]-undec-7-enium bromide, 5-octyl-7-methyl-1,5,7-triazabicyclo[4.4.0]dec-5-enium bromide; 5-2-ethylhexyl-7-methyl-1,5,7-triaza-5-azoniabicyclo[4.4.0]dec-5-enium bromide, 5-octyl-1,5-diazabicyclo[4.3.0]non-5-enium bromide; 5-2-ethylhexyl-1,5-diazabicyclo[4.3.0]non-5-enium bromide, or a combination thereof. See structures below.

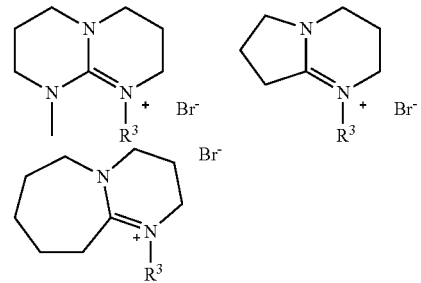

where $R^3$ is a is n-octyl or 2-ethylhexyl.

Alternatively, the iminium compound is an acyclic iminium compound that is not an acyclic guanidinium compound. Examples of acyclid iminium compounds include, but are not limited to $N^2,N^2$-2-ethylhexyloctyl-$N^1,N^1$-dimethylethanamidinium bromide, $N^2,N^2$-dioctyl-$N^1,N^1$-dimethylethanamidinium bromide, $N^2,N^2$-decyloctyl-$N^1,N^1$-dimethylethanamidinium bromide, $N^2,N^2$-dodecyloctyl-$N^1$,$N^1$-dimethylethanamidinium bromide, $N^2,N^2$-butyloctyl-$N^1,N^1$-dimethylethanamidinium bromide, $N^2,N^2$-undecyloctyl-$N^1,N^1$-dimethylethanamidinium bromide, and the chloride compounds of the above.

The iminium compound may be commercially available. For example, benzyl-1,8-diaza-bicyclo[5.4.0]undec-7-enium chloride is commercially available from Akzo Nobel of Norcross, Ga., U.S.A.

Iminium compounds may be made by the synthesis of an amidine-functional compound followed by alkylation at the $N^2$-nitrogen of the amindine-functional compound.

For example, polyazapolycycloalkene having amandine functionality can be reacted with an organofunctional compound such as an alkylhalide. Amidines may be produced by methods known in the art. For example, amidines may be formed by the reaction of the acetal or ketal of an amide with a primary amine.

The organofunctional compounds that may be reacted with the amidine-functional compound to make the iminium compounds include, but are not limited to, those of formula (V): $R^{12}R^{13}$, where each $R^{12}$ is an alkyl group or an aralkyl group; and each $R^{13}$ is halo selected from the group consisting of chloro, bromo, or iodo, alternatively chloro or bromo, alternatively chloro. Iminium compound with non-halide counterions, such as $HSO_4^-$, $HCO_3^-$, acetate, $SO_4^{2-}$, $CO_3^{2-}$, $PO_4^{3-}$ and $HPO_4^{2-}$, can be made by ion exchange with the iminium halide compound. Ion exchange methods are known in the art.

Alternatively, the organofunctional compound of formula (V) may be an alkyl halide such as an n-alkyl halide. Suitable alkyl halides include, but are not limited to, 2-ethylhexyl bromide, 1-bromooctane, 1-chlorooctane, 1-bromobutane, 1-chlorododecane and 1-bromododecane. The method may include heating the ingredients, for example, to a temperature ranging from 50° C. to 150° C. Alternatively, the alkyl halide may be selected from the group consisting of the bromine compounds listed above. Alternatively, the n-alkyl halide may be selected from the group consisting of the n-alkyl bromides listed above. Alternatively in formula (V), $R^{12}$ is an n-alkyl group of 1 to 12 carbon atoms, and $R^{13}$ is a halogen counter ion selected from Cl and Br. Alternatively, $R^{12}$ is an n-alkyl group of 1 to 12 carbon atoms, and $R^{13}$ is Cl. Alternatively, $R^{12}$ is an n-alkyl group of 1 to 12 carbon atoms, and $R^{13}$ is Br. The resulting reaction product comprises an iminium compound, such as an $N^2$-alkyl-polyazacyclokenium bromide or $N^2$-alkyl-polyazapolycycloalkenium bromide and a $N^2$-hydrogen-polyazacycloalkenium bromide salt or $N^2$-hydrogen-polyazapolycycloalkenium bromide salt; and this reaction product may be used as the phase transfer catalyst of ingredient c) in the method described above.

Model Reaction for Preparing $N^2$-Alkyl-diazapolycycloalkene Halides

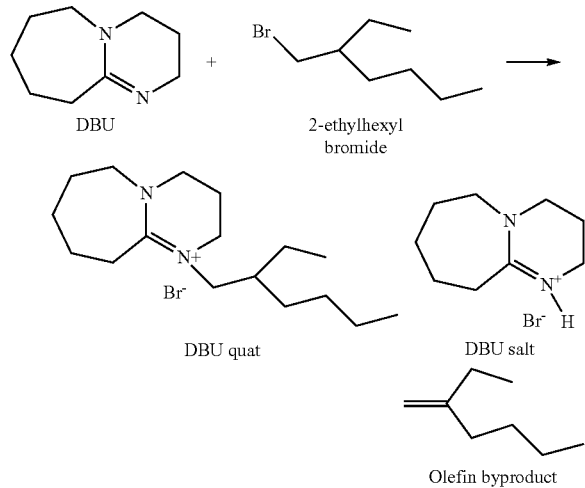

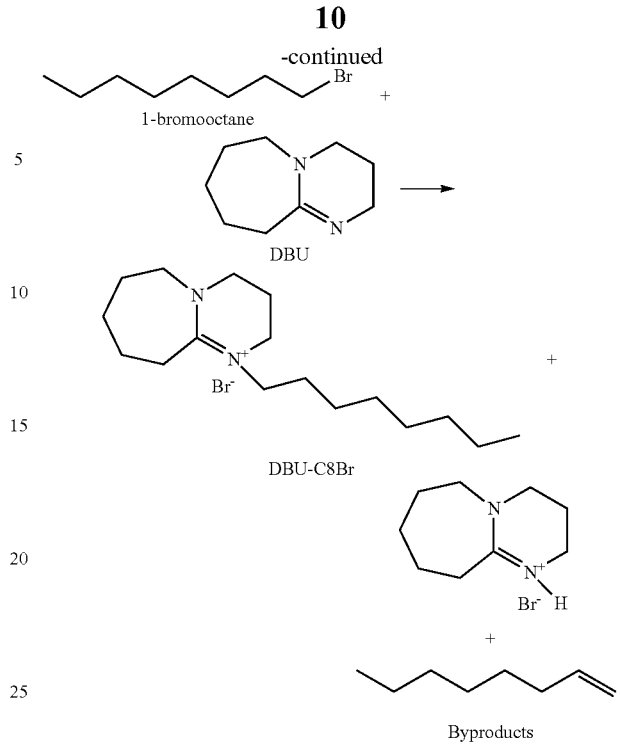

Byproducts

Alternatively, the method for preparing the reaction product comprising the iminium compound, such as the $N^2$-alkyl-polyazapolycycloalkene halide, described above may optionally further comprise purification of the iminium compound. Suitable purification methods are known in the art, for example, see "Synthesis and crystal structure of new phase-transfer catalysts based on 1,8-diazabicyclo[5.4.0]undec-7-ene and 1,5-diazabicyclo[4.3.0]non-5-ene", Progr. Colloid Polym. Sci. (2004) 123: 28-30). The $N^2$-alkyl-azaaxoniapolycycloalkene bromide (free of by-product(s) such as the salt and/or the olefin) may be used as the phase transfer catalyst of ingredient c) in the method described above.

The amount of the phase transfer catalyst added to the composition as ingredient c) depends on various factors including the types and amounts selected for ingredients a) and b), whether any additional ingredients, such as d) a co-catalyst, e) a solvent, f) a stabilizer, or a combination thereof, are added to the composition. However, the amount of the phase transfer catalyst added to the composition as ingredient c) may range from 0.1 mol % to 20 mol %, and alternatively 1 mol % to 10 mol %. Alternatively, the amount of phase transfer catalyst may range from 0.01 mol % to 15 mol %, alternatively 0.1 mol % to 10 mol %, alternatively 0.1 mol % to 7.5 mol %, and alternatively 2.5 mol % to 5 mol %.

Ingredient d), a co-catalyst, may optionally be used in the method for making a bis(alkoxysilylorgano) dicarboxylate or other ester-functional silanes described herein. The co-catalyst is selected based on various factors including the type of phase transfer catalyst selected for ingredient c). The co-catalyst has higher solubility than the PTC selected as ingredient c). Without wishing to be bound by theory, it is thought that the co-catalyst may increase the reaction rate for forming the bis(alkoxysilylorgano) dicarboxylate and other ester-functional silanes as compared to the reaction rate achievable using the same reaction conditions and the same ingredients except for omitting the co-catalyst. Without wishing to be bound by theory, it is thought that adding, as ingredient d), a salt bearing an anion of lower lipophilicity than the phase transfer catalyst of ingredient c) may provide the benefit of increasing reaction speed. It is further believed that in accordance to the theory of hard and soft acids and bases these harder anions demonstrate a lower affinity to the onium cation of the phase transfer catalyst in competition with the anion of the phase transfer catalyst, the nucleophile and the leaving group of the haloorgano group on ingredient a) while increasing the ionic strength of the composition. The amount of the co-catalyst may range from 0 mol % to 100% of the molar amount of the phase transfer catalyst of ingredient c). The co-catalyst of ingredient d) may be combined with ingredient c) or with ingredient b) before step 1) of the method described herein. Alternatively, ingredient d) may be added to the composition during step 1).

Exemplary co-catalysts for ingredient d) comprise metal compounds of formula $M^{c+}R^{14}$, where $M^{c+}$ is as described above and $R^{14}$ is selected from the group consisting of $HSO_4^-$, $HCO_3^-$, acetate, $SO_4^{2-}$, $CO_3^{2-}$, $HPO_4^{2-}$ and $PO_4^{3-}$. Exemplary co-catalysts for ingredient d) include metal acetates, such as potassium acetate and/or sodium acetate; metal sulfates such as $K_2SO_4$ and/or $Na_2SO_4$; metal hydrogen sulfates such as $KHSO_4$ and/or $NaHSO_4$; metal carbonates such as $K_2CO_3$ and/or $Na_2CO_3$; metal hydrogen carbonates such as $KHCO_3$ and/or $NaHCO_3$; or metal phosphates such as $K_2HPO_4$, $K_3PO_4$ and/or $Na_3PO_4$.

Ingredient e), a solvent, may optionally be used in the method for making an ester-functional silanes described herein. The solvent for ingredient e) may be combined with one or more of the ingredients described above before step i) of the method described herein. Alternatively, the solvent may be added during step i). The solvent may be a polar aprotic solvent, such as DMF, NMP, DMSO, or a combination thereof. The amount of solvent for ingredient d) may range from 10% to 200% based on the combined weight of all ingredients in the composition.

Alternatively, the reaction in step i) may be performed neat, i.e., without adding a solvent. Without wishing to be bound by theory, it is thought that ingredient a) and/or the product (e.g., acryloyloxysilane) may solubilize the ingredients to facilitate the reaction in the absence of an additional solvent.

Ingredient f), a stabilizer, may optionally be used in the method for making an ester-functional silane described herein. The stabilizer for ingredient f) may be combined with one or more of the ingredients described above before step i) of the method described herein. Alternatively, the solvent may be added during step i). The stabilizer for ingredient f) may be a stabilizer commonly used with acrylates, such as butylated hydroxytoluene (BHT), phenothiazine (PTZ), hydroquinone and derivatives thereof such as monomethyl ether of hydroquinone (MEHQ), and combinations thereof. Suitable stabilizers, such as those listed above are commercially available from Sigma-Aldrich, Inc. of St. Louis, Mo., U.S.A. The amount of stabilizer may range from 0 to 1500 ppmw, alternatively 10 to 1000 ppmw, based on the combined wt. of all ingredients in the composition.

The reaction in step i) may be performed by heating the composition at a reaction temperature up to 180° C. for a reaction time up to 18 hours. Alternatively, the reaction temperature may be up to 140° C. Alternatively, the reaction temperature may be up to 120° C. Alternatively, the reaction temperature may range from ambient to 180° C. Alternatively, the reaction temperature may range from 60° C. to 180° C. Alternatively, the reaction temperature may range from 130° C. to 180° C. Alternatively, the reaction temperature may range from 80° C. to 120° C. Alternatively, the reaction time may range from 30 min to 24 hours (h), alternatively 6 h to 18 h, alternatively 6 h to 12 h, alternatively 7 h to 11 h, and alternatively 14 h to 18 h.

The reaction may be performed under substantially anhydrous conditions. Substantially anhydrous conditions means that, the water content of the composition may range from 0 to 1% (w/w), alternatively from 0.15% to 1%, alternatively from 0.2 to 0.4%, based on the combined weight of the haloorganosilane of ingredient a), the metal salt of the carboxy-functional compound of ingredient b), and the phase transfer catalyst of ingredient c). The absence of water may be accomplished by removing traces of water from the ingredients in the composition. For example, the ingredients may be dried through the aid of a drying agent, such as molecular sieves. The method for preparing the ester-functional silane may optionally further comprise: drying one or more of the ingredients before step i). For example, this step may comprise drying ingredient b) and/or ingredient c) to reduce water content to a level of 1% or less, alternatively 0.05% or less, alternatively 0.025% or less, in the ingredient before heating in step i).

The reaction may be performed under substantially inert conditions. For example, step i) may be performed under an inert gas blanket, such as a nitrogen blanket.

When ingredient a) is a haloalkylalkoxysilane, and ingredient b) is a metal salt of a carboxylic acid, the reaction product comprises an ester-functional silane. A reaction occurs in step i) to form a reaction product comprising the ester-functional silane and a metal halide. The composition may optionally further comprise one or more additional ingredients. The additional ingredient is exemplified by, but not limited to, d) a co-catalyst, e) a solvent, f) a stabilizer, and a combination thereof. The method may further comprise step ii) removing at least a portion of the metal halide. The method may further comprise step iii) recovering the ester-functional silane.

The reaction in step i) of the method described above forms a reaction product comprising the ester-functional silane. The ester-functional silane typically has the formula $$Y_aSiQ_{(4-a)}, \qquad (VI)$$

where
a is 1 or 2; each Q is independently $R^1$ or $OR^1$, wherein each $R^1$ is as defined for ingredient a); Y is $R^{15}{}_2C=CH(CH_2)_dCOOR^{16}-$, wherein d is an integer from 0 to 18, alternatively 0 to 12, alternatively 8; each $R^{15}$ is independently H, a hydrocarbyl group, or $-(CH_2)_dCOOR^{10}SiQ_3$, wherein d is as defined above; and $R^{16}$ is a hydrocarbylene group having from 1 to 10 carbon atoms.

The hydrocarbylene groups represented by $R^{16}$ have from 1 to 10 carbon atoms, alternatively from 1 to 6 carbon atoms, alternatively from 1 to 3 carbon atoms. Examples of hydrocarbylene groups include, but are not limited to, alkylene, such as methylene, ethylene, propylene, 1-methylethylene, butylene, 1-methylpropylene, 2-methylpropylene, 11,-dimethylethylene, pentylene, 1-methylbutylene, 1-ethylpropylene, 2-methylbutylene, 3-methylbutylene, 1,2-dimethylpropylene, 2,2-dimethylpropylene, hexylene, heptylene, octylene, nonylene, decylene; and cycloalkylene, such as, cycloalkyl, such as cyclopentylene and cyclohexylene.

The hydrocarbyl groups represented by $R^{15}$ have from 1 to 18 carbon atoms, alternatively from 1 to 10 carbon atoms, alternatively from 1 to 3 carbon atoms. Acyclic hydrocarbyl groups containing at least three carbon atoms can have a branched or unbranched structure. Examples of hydrocarbyl groups include, but are not limited to, alkyl, such as methyl, ethyl, propyl, 1-methylethyl, butyl, 1-methylpropyl, 2-methylpropyl, 1,1-dimethylethyl, pentyl, 1-methylbutyl, 1-ethylpropyl, 2-methylbutyl, 3-methylbutyl, 1,2-dimethylpropyl, 2,2-dimethylpropyl, hexyl, heptyl, octyl, nonyl, and decyl; cycloalkyl, such as cyclopentyl and cyclohexyl; aryl, such as phenyl; alkenyl, such as vinyl, allyl, propenyl, butenyl, pentenyl, hexenyl, heptenyl, octenyl, nonenyl, and decenyl; and alkynyl, such as ethynyl, propynyl, butynly, pentynyl, hexynyl, septynyl, octynyl, nonynyl, and decynyl.

Examples of the ester-functional silane include, but are not limited to, methacryloyloxymethyldimethylmethoxysilane, γ-methacryloyloxypropylmethydimethoxysilane, γ-methacryloyloxypropyltrimethoxysilane, γ-methacryloyloxypropyltriethoxysilane, γ-methacryloyloxybutyldimethoxysilane, δ-methacryloyloxybutyltrimethoxysilane, δ-methacryloyloxybutylmethyldimethoxysilane, acryloyloxymethyldimethylmethoxysilane, γ-acryloyloxypropylmethyldimethoxysilane, γ-acryloyloxypropyltrimethoxysilane, γ-acryloyloxypropyltriethoxysilane, γ-acryloyloxypropylbutyldimethoxysilane, δ-acryloyloxybutyltrimethoxysilane, δ-acryloyloxybutylmethyldimethoxysilane, bis(γ-trimethoxysilylpropyl)fumarate, bis(γ-triethoxysilylpropyl)fumarate, bis(γ-trimethoxysilylpropyl)maleate, bis(γ-triethoxysilylpropyl)maleate, bis(γ-trimethoxysilylpropyl)itaconate, bis(γ-triethoxysilylpropyl)itaconate, -Stearyloxypropyltrimethoxysilane, -stearyloxymethyldimethoxymethylsilane, -palmityloxymethyltriethoxysilane, γ-methacryloyloxypropyltrimethoxysilane, -acryloyloxymethyltrimethoxysilane, γ-acryloyloxypropylmethyldimethoxysilane, 10-undecenoxymethyltrimethoxysilane, γ-10-undecenoxypropylmethyldimethoxysilane, γ-10-undecenoxypropyltrimethoxysilane, 10-undecenoxymethyltriethoxysilane, γ-10-undecenoxypropylmethyldiethoxysilane, 5-hexenoxymethyltrimethoxysilane, γ-5-hexenoxypropylmethyldimethoxysilane, γ-sorboxypropyltrimethoxysilane, sorboxymethyltrimethoxysilane, γ-sorboxypropyltriethoxysilane, and sorboxymethyldimethylethoxysilane.

The reaction product typically further comprises a first metal halide having formula (III): $M^{c+}X^-_c$ (III) where $X^-$ is a halide anion as defined for ingredient a), M is a metal atom as defined above for ingredient b, and subscript c is the valence of M as defined above for ingredient b).

The method described above may further comprise step ii): removing at least a portion of the first metal halide from the reaction product. As used herein, "a portion" means enough to reduce the metal halide in the reaction product to within the ranges described below. For example, a portion is typically at least 50%, alternatively at least 90%, alternatively at least 99.99%, of the initial amount of the metal halide in the reaction product.

The metal halide may be removed from the reaction product by processes known in the art for removing a solid metal halide from an organic material. The metal halide may be removed by, for example, filtering, centrifuging, decanting, washing, or a combination thereof. For example, the metal halide may be removed by filtration or decantation. Alternatively, the metal halide may be removed by decanting the ester-functional silane from the metal halide followed by washing with a solution, as described below.

After removing at least a portion of the metal halide from the reaction product, the ester-functional silane typically contains the metal halide in an amount less than 10,000 parts per million by weight (ppmw), alternatively from 1 to 1000 ppmw, alternatively from 10 to 100 ppmw, based on the weight of the ester-functional silane of the first metal halide.

Alternatively, removing at least a portion of the metal halide in step ii) may be performed by a method comprising washing a mixture comprising i) the reaction product formed in step i) (i.e., the reaction product comprising the ester-functional silane and the metal halide of formula (III)), and ii) a non-polar solvent with a solution comprising i) water and, optionally, ii) a second metal halide, to produce an organic phase comprising the ester-functional silane and an aqueous phase comprising at least a portion of the first metal halide (i.e., the metal halide of formula (III) formed by the reaction in step i)).

The non-polar solvent has a dielectric constant below 10, alternatively below 5, alternatively from 1 to 5. The non-polar solvent has a density less than 1.0 grams per milliliter (g/mL), alternatively from 0.6 to 0.9 grams per mL, alternatively from 0.7 to 0.8 g/mL, at 25° C. Examples of the non-polar solvents include, but are not limited to, organic solvents such as mineral spirits, toluene, m-, o-, and p-xylene and mixtures thereof, n-pentane, n-hexane, n-heptane, cyclopentane, cyclohexane, cyclooctane, cyclohexane, cis-cyclooctene, tert-butyl methyl ether and di-n-butyl ether.

The mixture may be formed by adding the non-polar solvent to the composition in step i). Alternatively, the mixture may be formed by combining the non-polar solvent with the reaction product comprising the ester-functional silane and the first metal halide in the reactor and with the conditions typically used for blending solutions. For example, the combining may be done at ambient temperatures in a mixing tank with a mixing blade.

The ester-functional silane is typically present in the mixture at an amount ranging from 1% to 90%, alternatively from 10% to 80%, alternatively from 30% to 70%, based upon the combined weight of the non-polar solvent, the ester-functional silane, and the first metal halide.

The non-polar solvent is present in the mixture at an amount ranging from 10% to 90%, alternatively 15% to 80%, alternatively 25% to 60%, based on the combined weight of the non-polar solvent, the ester-functional silane, and the first metal halide.

The first metal halide is typically present in the mixture at an amount ranging from 1% to 50%, alternatively 5% to 30%, alternatively 5% to 15%, based on the combined weight of the ester-functional silane, the non-polar solvent, and the first metal halide. The amount of the first metal halide in the mixture may be calculated stoichiometrically or determined by processes known in the art for determining the amount of a metal halide in a mixture, for example by ion chromatography.

The solution comprises a) water and, optionally, b) a second metal halide. For example, the solution may comprise an amount ranging from 0% to a less than a saturated concentration, alternatively from 0% to 50%, alternatively from 0 to 15%, based on the combined weight of the second metal halide and the water, of the second metal halide. As used herein, a "saturated concentration" means the concentration, at a particular temperature and pressure, at which no additional amount of the second metal halide will dissolve.

The water is typically deionized water; however, other types of water, such as distilled water or tap water, may be used.

The second metal halide is as described and exemplified above for the first metal halide of formula (III).

The second metal halide may be the same or different as the first metal halide and may be a mixture of metal halides, each according to the formula (III) herein. In one embodiment, the second metal halide is the same as the first metal halide and is potassium chloride or sodium chloride.

Examples of solutions useful in the second process of the invention include water and less than saturated aqueous solutions of sodium chloride, sodium bromide, potassium chloride, or potassium bromide.

When the solution comprises the second metal halide, the solution may be made by processes known in the art for making such solutions. Many aqueous solutions of metal halides are available commercially.

Step ii) in this embodiment may be conducted in any vessel known in the art for washing an organic solution with water. For example, step ii) may be conducted in a stainless steel tank equipped with mechanical mixing.

The time required for step ii) in this embodiment is equal to the time required to combine and mix the solution and the mixture and for the solution to extract the first metal halide from the mixture. For example, the time of required for step ii) in this embodiment is typically from 1 minute to 60 minutes, alternatively from 5 minutes to 45 minutes, alternatively from 10 minutes to 45 minutes.

The order and rate of addition of the solution in this embodiment is generally not critical. Typically the solution and mixture may be added at any rate and in any order.

The temperature at which step ii) in this embodiment is conducted is typically from 0 to 120° C., alternatively from 0 to 60° C., alternatively from 10 to 40° C.

The pressure at which step ii) in this embodiment is conducted is typically from sub-atmospheric to super-atmospheric pressures, alternatively from 0 to 1000 kPag, alternatively from 0 to 100 kPag, alternatively at atmospheric pressure.

The mixture is washed with a sufficient amount of the solution so the first metal halide and the second metal halide together are at least 15% (w/w), alternatively at least 18%, alternatively from 18 to 50% of the combined weight of the first metal halide, the second metal halide, and the water. As used herein, a "sufficient amount" is an amount that is not too great to cause the combined percentage of the first and second metal halide to be outside the prescribed limits. A sufficient amount of the solution may be calculated from the weight of the first metal halide in the mixture and the second metal halide and water in the solution, which may be determined using processes known in the art, for example by ion chromatography.

The washing produces an organic phase, comprising the ester-functional silaneester-functional silane and the non-polar solvent, and an aqueous phase, comprising the solution and at least a portion of the first metal halide. The organic and aqueous phases are immiscible.

The aqueous phase comprises at least 15%, alternatively at least 18%, alternatively from 18% to a saturated concentration, based on the weight of the first metal halide, the second metal halide, and the water, of the first metal halide and second metal halide combined.

After washing in step ii) in this embodiment, the ester-functional silane typically comprises less than 10,000 parts per million by weight (ppmw), alternatively from 1 to 1000 ppmw, alternatively from 10 to 100 ppmw, based on the weight of the ester-functional silane, of the first metal halide.

This embodiment provides relatively fast separation of the bis(alkoxysilyl)fumarate and metal halide (i.e., faster than filtration). Further, this embodiment eliminates the need for the filtration of the organic phase. Still further, this embodiment allows for washing the ester-functional silane without significant hydrolysis and without formation of a dispersion that is difficult to separate.

Alternatively, when an optional polar aprotic solvent for ingredient d) is used in step i) of the method described herein, the polar aprotic solvent is removed from the reaction product before adding the non-polar solvent. The polar aprotic solvent of ingredient d) can be removed by any convenient means, such as stripping or distillation under atmospheric or reduced pressure.

The method may optionally further comprise step iii): recovering the ester-functional silane. Step iii) may be performed during or after step ii) of the method described above. Recovering may be accomplished by processes known in the art. For example, recovering may be performed by a method comprising stripping or distillation at elevated temperature and/or reduced pressure. When the second embodiment is performed for step ii), the organic phase and the aqueous phase may be separated using known processes, such as by decantation, followed by distillation of the organic phase.

The ester-functional silanes prepared by the method described herein may be used as coupling agents for unsaturated resin or polymer systems, an adhesion promoter at organic-inorganic interfaces, and as a surface modifier.

The ester-functional silane prepared by the method described herein is particularly useful in engineered rubber goods applications. Such applications include belts and/or hoses. Alternatively, the ester-functional silane, prepared by the method described herein is particularly useful in tire applications, such as in a rubber composition used for preparing a tire, or a portion thereof, e.g., a tread. The rubber composition may be suitable for use in tires for various applications, e.g., race cars, heavy-vehicle applications such subway trains and buses, for tires for vehicles transporting heavy loads, construction vehicles, agricultural vehicles, 4×4 vehicles, passenger vehicles, vans, sport utility vehicles, aircraft, and/or motor vehicles. The rubber composition may be used in the manufacture of new tires and/or for re-treading worn tires. An exemplary such rubber composition typically comprises A) a diene polymer such as a polyisoprene, a polybutadiene, a polyvinylaromatic polymer, or a natural rubber, B) a reinforcing filler such as silica and/or carbon black and/or natural fibers, e.g., starch and/or cellulose, and C) an ester-functional silane, particularly bis(triethoxysilylpropyl)fumarate, prepared by the method described herein. The ester-functional silane, particularly the ester-functional silane, prepared by the method described herein may be added to a rubber composition as described in, for example, any one of U.S. Pat. Nos. 5,811,479; 6,071,995; 6,903,155; 6,900,263; 7,078,449; 7,186,776; 7,256,233; 7,300,970; 7,629,408; and 7,718,717; and PCT Publications WO 2010/000478, WO2010/125123, and WO2010/125124; in addition to, or instead of, the alkoxysilane and/or coupling agent in the rubber compositions described therein.

These examples are intended to illustrate some embodiments of the invention and should not be interpreted as limiting the scope of the invention set forth in the claims. Reference examples should not be deemed to be prior art unless so indicated. The following ingredients are used in the examples below.

| Raw Material (Abbreviated) | Raw Material Name | Supplier |
| --- | --- | --- |
| DBU | 1,8-Diazabicyclo[5.4.0]-undec-7-ene | Aldrich |
| MTBD | 7-methyl-1,5,7-triazabicyclo[4.4.0] dec-5-ene | Aldrich |

-continued

| Raw Material (Abbreviated) | Raw Material Name | Supplier |
|---|---|---|
| DBU-Octyl Bromine | DBU-octyl bromine (or DBU quat): Quaternary salt of DBU and octyl-bromine | prepared as described in the reference examples herein |
| DBU-Octyl Bromine/Potassium Acetate (KAc) | Potassium acetate and Quaternary salt of DBU and octyl-bromine | Mixture of DBU-Octyl Bromine prepared as above and KAc from Aldrich |
| TBAB | Tetratbutylammonium Bromide | Aldrich |
| TBA-Acetate | Tetrabutylammonium Acetate | Aldrich |
| TBA-Chloride | Tetrabutylammonium Chloride | Aldrich |
| TBA-Hydrogenosulfate | Tetrabutylammonium Hydrogenosulfate | Aldrich |
| TBAB/Potassium Acetate (KAc) | — | Mixture of TBAB and KAc, both from Aldrich |
| KAc | Potassium Acetate | Aldrich |
| CPTES | Chloropropyltriethoxysilane | DCC |
| Disodium Fumarate | — | Aldrich |
| Dipotassium Fumarate | — | MP Biomedicals, LLC. |
| PTZ | Phenothiazine | Aldrich |
| BHT | butylated hydroxytoluene; 2,6-bis(1,1-dimethylethyl)-4-methylphenol | Aldrich |

In the table above, 'Aldrich' refers to Sigma-Aldrich, Inc. of St. Louis, Mo., U.S.A. Chloropropyltriethoxysilane was commercially available as DOW CORNING@ Z-6376 from Dow Corning Corporation of Midland, Mich., U.S.A.

Reference Examples 1 to 8

General Procedure for Preparation of Quats

Polyazabicycloalkene quats: alkyl halide quats (iminium salts) were prepared by combining a polyazabicycloalkene (described above) and an alkyl halide. The alkyl halides tested were 2-ethylhexyl bromide, 1-bromobutane, 1-bromooctane, 1-bromododecane, and 1-chlorooctane. The combinations were heated in some instances. Synthesis of the resulting iminium salts is illustrated below for DBU+2-ethylhexyl bromide in the model reactions shown below. The competing reaction of elimination, to form an olefin by-product, accounted for 63% of the reaction mixture, leaving 37% DBU: ethylhexyl bromine quat. This reaction product can be used as a phase transfer catalyst for ingredient c) in the method described above without purification. Alternatively, purification of the DBU quat before use of said quat as the phase transfer catalyst of ingredient c) may be performed by any convenient means, as described above in the specification. Replacing the 2-ethylhexyl bromine with 1-bromooctane, as shown in the model reactions, below increased the yield of the resulting DBU: octylbromine quat to 98%. Other n-alkyl halides such as 1-chlorooctane, 1-bromobutane and 1-bromododecane were also reacted with DBU to form the corresponding iminium salt, suitable for use as a phase transfer catalyst.

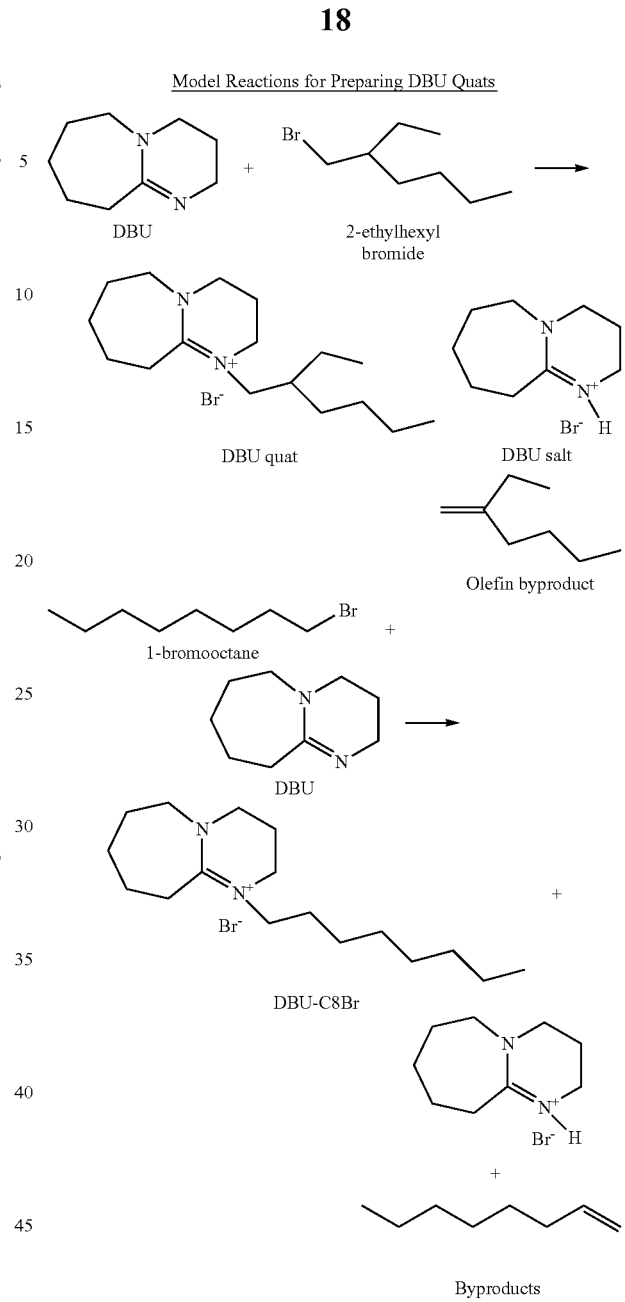

Model Reactions for Preparing DBU Quats

Reference Example 1

DBU 2-ethylhexyl Bromide Quat

To a 15 ml vial were added 3.03 g (19.9 mmol) of DBU and 3.84 g (19.9 mmol) of 2-ethylhexyl bromide. The vial was vortex mixed to form a clear solution and placed in an oven at 80° C., removed and briefly vortex mixed after 7 minutes then returned to the oven. The contents were hazy after 7 minutes. The vial was removed from the oven after 30 minutes. The contents separated into two phases, a thick lower phase and a thinner upper phase. $^1$H NMR showed the upper phase to be a mixture of starting materials and 2-ethylhexene. By $^1$H NMR, the crude material lower phase was 37% quat salt and the balance was DBU.HBr and a small amount of 2-ethylhexene. The crude material lower phase was evaluated as a phase transfer catalyst without purification. In a separate preparation, the crude product was purified by dissolution in methylene chloride, washing with deionized (DI) water, drying of the organic layer over MgSO$_4$, and addition of pentane to the organic layer to form two phases. The pentane layer, containing mostly 2-ethylhexene, was discarded. The methylene chloride layer was vacuum stripped to 50° C. @4 torr to isolate the pure quat salt.

Reference Example 2

MTBD 2-ethylhexyl Bromide Quat

To a 2 ml vial was added 0.48 g (3.1 mmol) of MTBD and 0.61 g (3.1 mmol) of 2-ethylhexyl bromide. The vial was vortex mixed to form a clear solution and placed in an oven at 104° C., removed and briefly vortex mixed after 14 minutes then returned to the oven. The contents were hazy/opaque after 14 minutes. An additional vortex mix was completed after 30 minutes. The vial was removed from the oven after 138 minutes. The contents separated into two phases, a thick lower phase and a thinner upper phase. 1H NMR showed the upper phase to be a mixture of starting materials and 2-ethylhexene. The crude material lower phase was evaluated as a phase transfer catalyst without purification.

Reference Example 3

DBU Octyl Bromine Quat

To a 500 ml 3 neck flask were added 193.67 g (1.00 mol) of 1-bromooctane. The flask was equipped with a paddle stirrer (202 rpm), a thermometer/N$_2$ headspace purge inlet, a water cooled reflux condenser/N$_2$ headspace purge outlet to oil filled bubbler and an addition funnel containing 152.73 g (1.00 mol) of DBU. The 1-bromooctane was heated with a heating mantle to 87° C. before the contents of the addition funnel were added dropwise over 30 minutes. The contents were cooled to 80° C. before transfer to a bottle. In a separate experiment, the order of addition was reversed and found to be inconsequential. $^1$H NMR showed only a trace (2%) of 1-octene was formed and no starting material remained (FIG. 24). The material was evaluated as a phase transfer catalyst without purification.

Reference Example 4

DBU Octyl Chloride Quat

To a 100 ml 3 neck flask were added 21.28 g (0.140 mol) of DBU and 20.77 g (0.140 mol) of 1-chlorooctane. The flask was equipped with a 1" magnetic stir bar, a thermometer/N$_2$ headspace purge inlet, and a water cooled reflux condenser/N$_2$ headspace purge outlet to oil filled bubbler. The contents were heated with a heating mantle and maintained at 120° C. for 3.3 hours. The contents were cooled to 80° C. before transfer to a bottle. $^1$H NMR showed only a trace (2%) of 1-octene was formed and no starting material remained. The material was evaluated as a phase transfer catalyst without purification.

Reference Example 5

MTBD Butyl Bromide Quat

At the ambient temperature, 1.80 g (11.3 mmol) of MTBD was mixed with 1.61 g (11.7 mmol) of 1-bromobutane. The reaction mixture was heated at 100° C. for 1 hour. After cooling down to the ambient temperature, a high viscosity dark-yellow clear liquid was isolated as the product. The product was analyzed with $^1$H NMR to verify that 1-bromobutane and MTBD were both reacted.

Reference Example 6

MTBD Octyl Bromide Quat

At the ambient temperature, 1.80 g (11.3 mmol) of MTBD was mixed with 2.26 g (11.7 mmol) of 1-bromooctane. The reaction mixture was heated at 100° C. for 1 hour. After cooling down to the ambient temperature, a high viscosity dark-yellow clear liquid was isolated as the product. The product was analyzed with $^1$H NMR to verify that 1-bromooctane and MTBD were both reacted. 1-Octene was detected at 4.8 mol % or 1.6 wt % content in the product.

Reference Example 7

MTBD Dodecyl Bromide Quat

At the ambient temperature, 1.60 g (10.4 mmol) of MTBD was mixed with 2.60 g (10.4 mmol) of 1-bromododecane. The reaction mixture was heated at 100° C. for 1 hour to form a viscous dark-yellow clear liquid. After cooling down to the ambient temperature, a yellow solid was isolated as the product. The product was analyzed with $^1$H NMR to verify that 1-bromododecane and MTBD were both reacted. 1-Dodecene was detected at 11.8 mol % or 5.3 wt % content in the product.

Reference Example 8

Synthesis of Acyclic Iminium Salt

A 50 mL 3 neck flask was equipped with magnetic stirbar, heating mantle, thermometer/temperature controller, Nitrogen headspace purge, and distillation head. To the flask was added in order, 9.90 g of 2-ethyl-1-hexylamine (77 mmol, CAS #104-75-6, FW 129.24, Aldrich) and 10.33 g N,N-dimethylacetamide dimethyl acetal (78 mmol, CAS #18871-66-4, FW 133.19, Aldrich). The contents were heated and within 6 minutes exothermed to a temperature of 74° C. The contents were maintained at 68° C. for an additional hour before vacuum stripping to 70° C. at 3 Torr. A total of 13.37 g was transferred to a vial, 88% isolated yield. The material was characterized by GC/MS and NMR as N$^2$-2-ethylhexyl-N$^1$,N$^1$-dimethylethanamidine.

A 25 mL 3 neck flask was equipped with magnetic stirbar, heating mantle, thermometer/temperature controller, Nitrogen headspace purge, and water cooled reflux condenser. To the flask were added 5.98 g of amidine prepared above (30 mmol, FW 198) and 5.83 g of 1-octylbromide (30 mmol, FW 193.13, Aldrich). The contents were heated to 150° C. and held at this temperature for 90 minutes. $^1$H NMR analysis at this time showed no remaining starting material, 83 mol % of the 1-octyl bromide had been converted to iminium salt N$^2$,N$^2$-2-ethylhexyloctyl-N$^1$,N$^1$-dimethylethanamidinium bromide and 17 mol % to 1-octene.

Example 1

Synthesis of Bis(triethoxysilylpropyl) Fumarate Using Different Phase Transfer Catalysts Model Reaction Scheme 1.
Synthesis of bis(triethoxysilylpropyl) fumarate during the condensation of chloropropyltriethoxysilane and disodium fumarate.

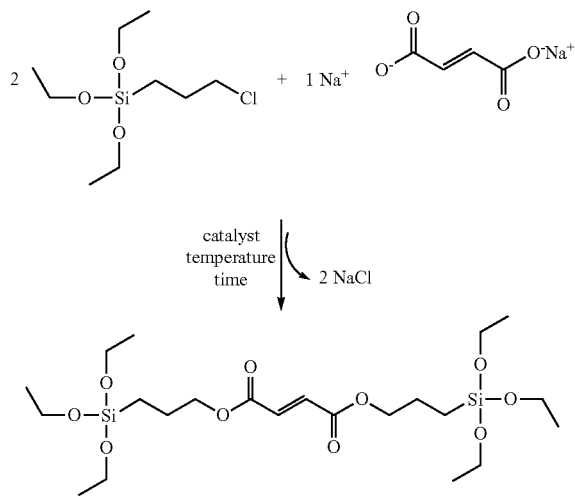

Bis(triethoxysilylpropyl)fumarate was synthesized with a selection of phase transfer catalysts (PTC) during the condensation of CPTES and disodium fumarate. The condensation reaction was performed by catalyzing the reaction of chloropropyltriethoxysilane (2.38 mL, 10 mmol) and disodium fumarate (0.80 g, 5 mmol) with a selection of catalysts shown below in the table. Each sample was formulated with amounts of CPTES and PTC at a molar ratio of 20:1 (CPTES:PTC ratio, mmol:mmol) or 5 mole % CPTES. The reactions were conducted at temperatures ranging from 120° C. to 140° C. for 6 to 18 hours. The closed reactions were conducted in borosilicate glass vials with overhead stirring at 300 rpm at ambient pressure in a Freeslate parallel pressure reactor (Sunnyvale, Calif.). The resultant reaction product was a liquid with a salt precipitate, which was quantitatively analyzed by Gas Chromatography.

The retention times of the materials of interest were 9.242 min for CPTES and 15.350 min for the bis-fumarate. Refer to Table 1-2. The CPTES and bis-fumarate peaks were confirmed by GC-MS.

Encompassing experimental and instrumental errors, the relative standard deviation of the measurements was less than 1%.

TABLE 1

Phase Transfer Catalysts.

| Catalyst | Catalyst Source | Amount (0.5 mmol) | CPTES: Catalyst |
|---|---|---|---|
| 1,8-Diazabicyclo[5.4.0]- undec-7-ene; DBU | Aldrich | 76.1 mg | 20:1 mmol/mmol |
| DBU-Octyl Bromine Quat | Reference Example 4 | 172.7 mg | 20:1 mmol/mmol |
| DBU-Octyl Bromine/Potassium acetate, 1:1 mol | Mixture of the quat prepared in Reference Example 4 and & KAc purchased from Aldrich | 172.7 + 49.0 mg | 20:1 mmol/mmol |
| Tetrabutylammonium bromide, TBAB | Aldrich | 161.3 mg | 20:1 mmol/mmol |
| Tetrabutylammonium acetate; TBA-Acetate | Aldrich | 150.8 mg | 20:1 mmol/mmol |
| Tetrabutylammonium chloride; TBA-Chloride | Aldrich | 139.0 mg | 20:1 mmol/mmol |
| Tetrabutylammonium hydrogenosulfate; TBA-Hydrogenosulfate | Aldrich | 169.8 mg | 20:1 mmol/mmol |
| Tetrabutylammonium bromide/Potassium acetate, 1:1 mol | Mixture of compounds purchased from Aldrich | 163.1 + 49.0 mg | 20:1 mmol/mmol |

"Aldrich" in the table above refers to Sigma-Aldrich Inc.

TABLE 1-2

PTC-catalyzed Synthesis of Bis(triethoxysilylpropyl) Fumarate (mg/mL).

| Catalyst | 140° C., 6 h 6 h | 120° C., 18 h 18 h |
|---|---|---|
| 1,8-Diazabicyclo[5.4.0] undec-7-ene; DBU | 502 | 299 |
| DBU-Octyl Bromine Quat | 634 | 498 |
| DBU-Octyl Bromine/ Potassium acetate, 1:1 mol | 885 | 509 |
| Tetrabutylammonium bromide, TBAB | 258 | 300 |
| Tetrabutylammonium acetate; TBA-Acetate | 263 | 325 |
| Tetrabutylammonium chloride; TBA-Chloride | 290 | 626 |
| Tetrabutylammonium hydrogenosulfate; TBA-Hydrogenosulfate | 404 | 648 |
| Tetrabutylammonium bromide/Potassium acetate, 1:1 mol | 192 | 278 |

Comparative Example 1

Synthesis of Bis(Triethoxysilyl Propyl) Fumarate with DBU

Disodium fumarate (93.0 g; 0.581 mol), CPTES (280.0 g; 1.16 mol), PTZ and BHT (0.112 g/each) and DBU (3.52 g) were sequentially added to a 500 ml round bottom (RB) flask equipped with a mechanical agitator. The reaction mixture was heated at 140° C. for 18 hr. After bodying (i.e., let sit) for 2 days, 191.3 g of clear brownish supernatant was decanted. Then 180 ml of hexanes was added to the salt residue to form a slurry. After forming the slurry, 480 g of 15% brine was added and mixed. After 30 min settlement, 224.5 g of clear organics were separated and vacuum stripped to give 82.6 g of a clear brownish liquid with low volatility. The two clear brownish liquids were combined and subject to a simple distillation under vacuum (less than 1 torr) at 140° C. The bis(triethoxysilylpropyl)fumarate product (238.3 g) was isolated in 92% yield. This example shows the speed and ease that the metal halide may be removed from bis(triethoxysilylpropyl)fumarate using the process of the invention.

Example 2

Comparison of Different PTCs

The phase transfer catalysis reaction between disodium fumarate and CPTES was found to be an effective synthetic route for making bis(3-triethoxysilylpropyl)fumarate. The reaction was a solid-liquid bi-phasic necleophilic substitution. It was sluggish due to inefficient material transfer through the solid-liquid interface or interphase. To gain an acceptable conversion, a high reaction temperature and a prolonged reaction time were employed. Under these conditions, choice of catalyst and solvent affected the reaction rate. The effects of the catalysts and solvents were studied using the following general experimental procedure.
1) Under a nitrogen blanket, to a 150 mL RB flask were loaded disodium fumarate and CPTES at 1:2 molar ratio, 500 ppm of BHT and PTZ stabilizers, a phase transfer catalyst, and optionally, a solvent.
2) The reaction mixture was heated to 140° C. under agitation.
3) The liquid phase was sampled for gas chromatography (GC) analysis after 3 h and 18 h. The GC peak areas of bis(3-triethoxysilylpropyl)fumarate and CPTES were used to calculate the GC area % of bis(3-triethoxysilylpropyl)fumarate using the equation "GC Area % of Bis (3-triethoxysilylpropyl)fumarate=(GC Peak Area of Bis (3-triethoxysilylpropyl)fumarate)/(GC Peak Area of Bis (3-triethoxysilylpropyl)fumarate+GC Peak Area of CPTES)×100%".
4) Four PTC's, i.e., tetrabutylammonium bromide (TBAB), tetrabutylphosphonium bromide (TBPB), DBU, and DBU octyl bromine quat; and two solvents (mineral spirit and DMF), were evaluated in six runs. The catalysts were added at 2 mol % or 4 mol % of the moles of CPTES. Mineral spirit is a non-polar solvent. DMF is a high polarity aprotic solvent. The solvents were added at a certain percentage of the weight of the reaction mixture. The calculated GC area % of bis(3-triethoxysilylpropyl) fumarate is compiled in the table below for these six runs. The GC area % was qualitatively aligned to the actual reaction conversion, but could not be treated equally as the reaction conversion because bis(3-triethoxysilylpropyl)fumarate and CPTES have different GC response factors and affinities with the solid salts. Bis(3-triethoxysilylpropyl)fumarate seemed to have a lower GC response factor, and a lower affinity with the solid salts, than CPTES.

TABLE 2-1

The GC area % of bis(3-triethoxysilylpropyl)fumarate at 140° C.

| Batch # | Catalysts | Solvents | GC Area % 3 hr | 18 hr |
|---|---|---|---|---|
| 1 | 4 mol % TBAB | Mineral spirit at 43 wt % | 4.2 | n/a |
| 2 | 4 mol % TBAB | None | 10.8 | 5.0 |
| 3 | 2 mol % DBU | None | 9.0 | 33.0 |
| 4 | 2 mol % DBU | DMF at 27 wt % | 15.8 | 79.4 |
| 5 | 2 mol % TBPB | None | 11.2 | 35.8 |
| 6 | 2 mol % DBU octy Br quat | None | 0.033 | 47.8 |

All the GC area % values in 3 hours were low, suggesting that the reaction was sluggish even at 140° C. and in the presence of catalysts. When 4 mol % of TBAB was used as the catalyst in Batch 2, the GC area % of bis(3-triethoxysilylpropyl)fumarate decreased from 10.8% in 3 hours to 5.0% in 18 hours. This resulted from quick degradation of TBAB in the first 3 hours at 140° C., as evidenced with a strong GC signal of the degradation product, tributylamine. Thus, TBAB was not a suitable catalyst for synthesis of bis(3-triethoxysilylpropyl)fumarate under these conditions. In the non-polar solvent, mineral spirit, in Batch 1, the reaction rate was further reduced as the GC area % was only 4.2% after 3 hours. Thus, a non-polar solvent was deemed detrimental to the reaction rate under these conditions. When the high temperature catalyst TBPB was used in Batch 5, the conversion was comparable to that of TBAB in 3 hours, but much higher than that of TBAB in 18 hours, indicating that TBPB was a better catalyst than TBAB for preparation of bis(3-triethoxysilylpropyl)fumarate under these conditions. DBU gave similar GC area % as TBPB in both 3 and 18 hours in Batch 3, suggesting that DBU was as efficient as TBPB. When 2 mol % of DBU octyl bromine quat was used as the catalyst in Batch 6, the conversion was low in 3 hours, but higher than those of DBU and TBPB in 18 hours. Without wishing to be bound by theory it is thought that there probably was an activation mechanism for DBU octyl bromine quat, and once activated, it was more efficient than DBU and TBPB. The most significant conversion gain in this example was achieved by doing the DBU-catalyzed reaction in the high polarity aprotic solvent, DMF, in Batch 4. There was a marginal lead of the GC area % in 3 hours and a remarkable superiority in 18 hours. Without wishing to be bound by theory, it is thought that the high GC area % in 18 hours could be attributed to an increased reaction rate, and a reduced association of bis(3-triethoxysilylpropyl)fumarate and CPTES with the solid salts in DMF. Therefore, it is thought that a high temperature catalyst, a high polarity aprotic solvent, or a combination thereof, can be used to improve the reaction conversion.

Example 3

Purification of Bis(triethoxysilylpropyl) Fumarate

Two batches of bis(triethoxysilylpropyl)fumarate prepared above in example 3, 3 and 6, were purified using a brine wash procedure as follows.
1) The reaction mixture was allowed to stand for 2 days at the room temperature. During the period, the salts settled to form a clean solid-liquid interface
2) After the clear brownish organics (the 1$^{st}$ portion of crude product) was decanted, hexanes was added to the resulting salt cake, and the mixture was re-slurrified. Then a brine was added to dissolve or partially dissolve the salts to form a saturated NaCl solution. Water can be used in place of the brine as long as the resultant brine phase is near saturation. The amount of hexanes should be sufficient to allow a quick liquid-liquid phase separation.
3) Once agitation stopped, the light organic phase quickly separated from the heavy brine phase to give a clean liquid-liquid interface within a few minutes.
4) The organic phase was evaporated under vacuum to remove hexanes, giving a brownish liquid (the second portion of crude product).
5) The two portions of crude product were combined and distilled at the pot temperature of 140° C. under vacuum (0.1 torr) to remove unreacted CPTES.
6) The product was isolated from the pot as a brownish low viscosity liquid. The purity of the product was determined with GC-FID (FIG. 1), and verified with $^1$H NMR (FIG. 2) to be 95%. The $^1$H NMR spectrum has the key features, including the unique chemical shift of the protons on the fumarate double bond, of the $^1$H NMR of bis(3-trimethoxysilylpropyl)fumarate.
7) The structure of the bis(3-triethoxysilylpropyl)fumarate molecule was confirmed with $^{13}$C and $^{29}$Si NMR (FIGS. 3 and 4), and GC-MS.

This resulted in the isolation of bis(3-triethoxysilylpropyl)fumarate with 95% purity in 92% yield in Batch 3, and in 91% yield in Batch 6. The impurities consisted of 3.8% of CPTES and 0.8% of the by-products identified with GC-MS (FIG. 5).

Example 5

Reaction of Sodium Acrylate Formed In Situ with 3-Chloropropyltriethoxysilane 66.4 g of 21% (w/w) NaOEt solution were added to 15.5 g (0.215 mol) acrylic acid to make "basic" sodium acrylate in situ in a flask. The basicity was indicated using phenolphthalein. The basic Na acrylate was agitate for 1 hr at RT. Next, 0.021 g of BHT and PTZ were added to the flask containing the basic sodium acrylate. After the BHT addition, 0.00365 mol (1.7 mol %) catalyst were added (i.e., 1.18 g TBAB, 0.96 g Dried HTA-1, 1.26 g DBU octylquat bromide quat dissolved in 5.0 g ethanol, or 1.27 g MTBD octylbromide quat dissolved in 5.0 g ethanol) followed by the addition of 51.7 g (0.215 mol) of CPTES and 36.6 g xylenes. This mixture was then heated to 120° C. while distilling out ethanol. Samples were taken for GC at 0, 0.5, 1, 2, 3, 4 and 5 hr at 120° C. The plot of conversion versus time for the 4 experiments is shown below in Table 5-1. HTA-1 and TBAB were run as comparative examples. The plot shows the advantage in reaction rate of using the preformed DBU and MTBD, octyl bromides as PTC.

TABLE 5-1

% conversion with different phase transfer catalysts.

| Time (hrs) | TBAB | HTA-1 | DBU-octyl bromide | MTBD-octyl bromide |
|---|---|---|---|---|
| 0 | 2.5 | 2.9 | 33.0 | 5.4 |
| 0.5 | 21.2 | 23.1 | 58.3 | 58.1 |
| 1 | 40.9 | 40.1 | 75.6 | 82.4 |
| 2 | 63.0 | 60.5 | 89.9 | 92.8 |
| 3 | 79.2 | 72.4 | 95.1 | 95.6 |
| 4 | 89.0 | 79.9 | 95.2 | 96.0 |
| 5 | 93.3 | 84.6 | 95.2 | 96.3 |

Comparative Example 2

Synthesis of Ester-Functional Silane ($CH_2$=CH$(CH_2)_8COOCH_2Si(OMe)_3$) Using TBAB A 1 L 3 neck flask was equipped with paddle stirrer, heating mantle, thermometer/temperature controller, Nitrogen headspace purge, and reflux condenser. The sodium undecenylate was purchased from MP Biomedicals (500 g size) and dried by placing the bottle without lid in a 105° C. oven overnight. To the flask was added in order, 4.87 g of tetrabutylammonium bromide (TBAB, 15 mmol, FW 322.37), 231.38 g of sodium undecenylate (1.12 mol, FW 206.3) and 190.86 g chloromethyltrimethoxysilane (1.12 mol, FW 170.6, Gelest) and 307.10 g toluene solvent (Aldrich). The contents were heated to a setpoint of 110° C. and held for 6 hours. Conversion by GC analysis; 0.5 hr 38.4%, 1 hr 64.6%, 2 hr 78.5%, 3.5 hr 86.3%, 5.3 hr 88.9%. The contents were pressure filtered through a bed of 560 coarse Celite filter aid on top of a 10 micron membrane. The material was then refiltered through a bed of 545 Celite on a 5 micron membrane. The toluene was vacuum stripped followed by distillation of the product, $CH_2$=CH$(CH_2)_8COOCH_2Si(OMe)_3$, 118° C. at 1 Torr. By GC analysis the 272.4 g distillation cut (76% yield) contained 0.23% tributylamine and 1.92% butylundecenoate impurities from decomposition of the TBAB during distillation.

Comparative Example 3

Synthesis of Ester-Functional Silane ($CH_2$=CH$(CH_2)_8COOCH_2Si(OMe)_3$) Using TBAB A 1 L 3 neck flask was equipped with paddle stirrer, heating mantle, thermometer/temperature controller, Nitrogen headspace purge, and reflux condenser. The sodium undecenylate was purchased from MP Biomedicals (500 g size) and dried by placing the bottle without lid in a 105° C. oven overnight. To the flask was added in order, 6.28 g of tetrabutylammonium bromide (TBAB, 19 mmol, FW 322.37), 249.42 g of sodium undecenylate (1.21 mol, FW 206.3) and 206.16 g chloromethyltrimethoxysilane (1.21 mol, FW 170.6, Gelest) and 268.7 g toluene solvent (Aldrich). The contents were heated to a setpoint of 110° C. and held for 3.8 hours. The material was filtered through a bed of 545 Celite on a 5 micron membrane. The toluene was vacuum stripped followed by distillation of the product, $CH_2$=CH$(CH_2)_8COOCH_2Si(OMe)_3$, 118° C. at 1 Torr. By GC analysis the 337.4 g distillation cut (88% yield) contained 1.21% tributylamine and 1.59% butylundecenoate impurities from decomposition of the TBAB during distillation. The material was characterized by GC/MS and NMR. MS characterization, m/z (relative abundance): 318 m/z (0.1%, M$^+$), 287 (40.6), 286 (19.0), 245 (13.4), 231 (14.1), 207 (75.6), 194 (35.9), 175 (85.6), 162 (51.6), 151 (23.7), 121 (100, base peak). $^{29}$Si NMR peak at −53.5, $^{13}$C NMR peaks at 173.9 ppm, 139.0, 114.2, 50.8 (3 carbons), 50.4, 34.0, 33.8, 28.4, 29.3, 29.2, 29.1, 29.1, 25.1. $^1$H NMR was also consistent with the structural assignment.

Comparative Example 4

Synthesis of Ester-Functional Silane ($CH_2$=CH$(CH_2)_8COO(CH_2)_3Si(OMe)_3$) Using TBAB A 1 L 3 neck flask was equipped with paddle stirrer, heating mantle, thermometer/temperature controller, Nitrogen headspace purge, and reflux condenser. The sodium undecenylate was purchased from MP Biomedicals (500 g size) and dried by placing the bottle without lid in a 105° C. oven overnight. To the flask was added in order, 6.31 g of tetrabutylammonium bromide (TBAB, 19.6 mmol, FW 322.37), 240.46 g of sodium undecenylate (1.16 mol, FW 206.3) and 256.05 g 3-chloropropyltrimethoxysilane (1.13 mol, FW 226.5, Dow Corning) and 251.45 g toluene solvent (Aldrich). The contents were heated to a setpoint of 110° C. and held for 6 hours. The material was filtered through a 10 micron membrane. The toluene was vacuum stripped followed by distillation of the product, $CH_2$=CH$(CH_2)_8COOCH_2CH_2CH_2Si(OMe)_3$, 147-156° C. at 1-2 Torr. By GC analysis the distillation cut contained high levels of tributylamine and butylundecenoate impurities from decomposition of the TBAB during distillation. Upon redistillation to remove these impurities, 269.5 g of product was obtained (69% yield). The material was characterized by GC/MS and NMR. MS characterization, m/z (relative abundance): 318 m/z (0.1%, M+), 287 (40.6), 286 (19.0), 245 (13.4), 231 (14.1), 207 (75.6), 194 (35.9), 175 (85.6), 162 (51.6), 151 (23.7), 121 (100, base peak). $^{29}$Si NMR peak at −42.7, $^{13}$C NMR peaks at 173.9 ppm, 138.7, 113.9, 65.8, 50.2 (3 carbons), 34.0, 33.5, 29.1, 28.9, 28.8, 28.8, 28.7, 24.7, 21.8, 5.1. $^1$H NMR was also consistent with the structural assignment.

Comparative Example 5

DBU as Phase Transfer Catalyst

To a 250 mL flask was added 0.05 g of phenothiazine (PTZ) and 0.05 g 2,6-bis(1,1-dimethylethyl)-4-methylphenol (BHT) to act as polymerization inhibitors, 19.2 g (0.204 mol) of sodium acrylate (Aldrich Chemical Co.), 35 g Xylenes, 48.5 g (0.201 mol) of 3-chloropropyltriethoxysilane (CPTES, Z-6376, Dow Corning) and 0.00342 mol of DBU. The contents were heated to a reaction temperature of 120° C., at which time (t=0, 0.5, 1, 2, 3, 5 hours) an aliquot was removed for GC analysis. Analysis of the crude reaction product was done by GC/MS and conversion was calculated using the uncorrected areas of CPTES and 3-(acryloxy) propyltriethoxysilane (gATE), gATE/(gATE+CPTES). The table of conversion versus time are shown below in Table 5-2.

TABLE 5-2

Results using DBU as catalysts.

| Time (hrs) | DBU |
|---|---|
| 0 | 0.0 |
| 0.5 | 3.0 |
| 1 | 13.0 |
| 2 | 40.7 |
| 3 | 56.9 |
| 5 | 71.7 |

Example 6

Synthesis of Ester-Functional Silane (CH$_2$=CH(CH$_2$)$_8$COOCH$_2$Si(OMe)$_3$) Using DBU-Octyl Bromide The procedure of comparative example 2 was repeated but with a change in PTC from TBAB to DBU-octyl bromide. The molar ratio of reactants and PTC were the same as in comparative example 2 but the scale was reduced. A 500 mL 3 neck flask was equipped with paddle stirrer, heating mantle, thermometer/temperature controller, Nitrogen headspace purge, and reflux condenser. The sodium undecenylate was purchased from MP Biomedicals (500 g size) and dried by placing the bottle without lid in a 105° C. oven overnight. To the flask was added in order, 2.48 g of DBU-octyl bromide (6.3 mmol, FW 391.13), 95.25 g of sodium undecenylate (0.46 mol, FW 206.3) and 78.39 g chloromethyltrimethoxysilane (0.46 mol, FW 170.6, Gelest) and 125.27 g toluene solvent (Aldrich). The contents were heated to a setpoint of 110° C. and held for 5 hours. Conversion by GC analysis; 1 hr 75.6%, 2 hr 97%, 3.5 hr 100%. The contents were pressure filtered through a 10 micron membrane. The toluene was vacuum stripped followed by distillation of the product, CH$_2$=CH(CH$_2$)$_8$COOCH$_2$Si(OMe)$_3$, 118° C. at 1 Torr. By GC/MS analysis the 130.93 g distillation cut (90% yield) contained no impurities from decomposition of the DBU-octyl bromide during distillation.

Example 7

Synthesis of Ester-Functional Silane Using Acyclic Iminium Compound as PTC

To a 250 mL 3 neck flask equipped with temperature controller, N$_2$ headspace purge, 1" magnetic stir bar and water cooled reflux condenser was added 1.46 g of the acyclic iminium salt prepared in reference example 8 and used without purification, (FW 391.13 g/mol, 3.7 mmol), 19.3 g sodium acrylate (Aldrich, FW 94, 205 mmol), 48.5 g 3-chloropropyltriethoxysilane (DC, FW 240.6, 202 mmol) and 35.29 g toluene solvent containing BHT and phenothiazine at a level of 680 ppm for each. The contents were heated to 120° C. 3-acryloxypropyltriethoxysilane was formed and characterized by GC/MS and NMR.

Example 8

Comparison of Different Alkyl Halide Iminium Salts of MTBD

The same equipment, processes, and reaction conditions were used as described in Comparative Example 5 but with the butyl, octyl, and dodecyl alkyl halide iminium compounds of MTBD used as the phase transfer catalysts. The table of conversion versus time is shown below in Table 8-1.

TABLE 8-1

Comparison of different alkyl halide iminium salts of MTBD

| Time (hrs) | MTBD butyl bromide | MTBD octyl bromide | MTBD dodecyl bromide |
|---|---|---|---|
| 0 | 0.6 | 1.5 | 3.1 |
| 0.5 | 26.8 | 35.8 | 43.8 |
| 1 | 44.3 | 59.9 | 65.6 |
| 2 | 65.2 | 73.5 | 74.9 |
| 3 | 74.2 | 84.8 | 79.0 |
| 5 | 80.7 | 87.8 | 83.4 |

Example 9

The Same Reaction Condition and Equipment were Used as in Comparative Example 5 Except Different DBU Iminium Salts were Used as PTC In this example xylenes were omitted from the reaction mixture for four of the reactions but included for two reactions to show that use of the iminium salt catalysts brings the added benefit of minimal decrease in PTC efficiency when a non-polar solvent (Xylenes) is used as a process aid. A small increase in efficiency was observed when the polar solvent N-methylpyrrolidone (NMP) was used. DBU-iso-C8Br PTC is from the reaction of DBU with 2-ethylhexyl bromide, all other PTC's were prepared from the corresponding n-alkyl (C4=butyl, C8=octyl, C12=dodecyl) bromide or chloride as noted in the graph legend. The table of conversion versus time are shown below in Table 9-1.

TABLE 9-1

Comparision of different DBU iminium compounds with and without solvent.

| Time (hrs) | DBU-iso-C8Br, no solvent | DBU-C12Br, no solvent | DBU-C4Br, no solvent | DBU-C8Br, no solvent | DBU-C8Br, Xylene solvent used | DBU-C8Cl, Xylene solvent used | DBU-C8Br, NMP solvent used |
|---|---|---|---|---|---|---|---|
| 0 | 6.4 | 7.8 | 2.0 | 6.8 | 11.5 | 3 | 8.4 |
| 0.5 | 62.3 | 58.9 | 43.7 | 55.8 | 49.4 | 50.8 | 74 |
| 1 | 74.6 | 74.1 | 69.1 | 70.5 | 67.8 | 69.2 | 82.5 |
| 2 | 82.0 | 82.8 | 80.6 | 77.7 | 80.2 | 81.7 | 87.7 |
| 3 | 84.8 | 85.8 | 84.1 | 82.3 | 84.5 | 85.7 | 90.1 |
| 5 | 88.0 | 88.5 | 85.6 | 85.9 | 87.7 | 89.2 | 92.3 |

Example 10

Use of Potassium Acrylate in Model Reaction

The same reaction conditions and equipment and processes were used as in Comparative Example 5 except that potassium acrylate was used instead of sodium acrylate and TBAB and the iminium salts of MTBE and DBU were used as PTC. The table of conversion versus time is shown below in Table 10-1.

TABLE 10-1

Conversion times with potassium acrylate in model reaction.

| Time (hrs) | MTBD-C8Br, xylenes solvent | DBU-C8Br, xylenes solvent | TBAB, xylenes solvent |
|---|---|---|---|
| 0 | 13.9 | 7.5 | 28.2 |
| 0.5 | 97.5 | 80.7 | 79.8 |
| 1 | 99.6 | 94.9 | 83.5 |
| 2 | 100.0 | 99.4 | 84.8 |
| 3 | 100.0 | 99.9 | 85.1 |
| 5 | 100.0 | 100.0 | 85.1 |

INDUSTRIAL APPLICABILITY

It was found that some of the phase transfer catalysts described herein as ingredient c) and/or the combination of the phase transfer catalyst of ingredient c) and the co-catalyst of ingredient d), can be used to produce a ester-functional silane at a lower temperature and/or a faster reaction time than conventional phase transfer catalysts. The catalysts described herein may also produce the ester-functional silane with fewer byproducts than when hexaethylguanidinium bromide is used as the catalyst with the same haloalkylalkoxysilane and carboxy metal salt. Finally, the ester-functional silanes produced by the method of the invention may have benefits in synthesizing new molecules and as adhesion promoters, coupling agents, and surface modifiers.

The invention claimed is:

1. A method for producing a reaction product comprising an ester-functional silane, the method comprising: i) reacting a composition comprising:
   a) a haloorganosilane,
   b) a metal salt of a carboxy-functional compound, where the metal salt of a carboxy-functional compound has the formula $[R^2COO^-]_c[M^{c+}]$ (II), wherein $R^2$ is substituted or unsubstituted hydrocarbyl having from 2 to 20 carbon atoms, each $M^{c+}$ is an alkali metal cation, alkaline earth metal cation, or ammonium cation and c is 1 or 2,
   c) a phase transfer catalyst comprising a polyazabicycloalkene, an $N^2$-alkyl-polyazapolycyclo-alkenium compound, or a mixture thereof, and
   d) a co-catalyst, where the co-catalyst comprises a compound of formula: $M^{c+}R^{14}$, where $M^{c+}$ is alkali metal cation or alkaline earth metal cation, c is 1 or 2, and $R^{14}$ is a counter ion selected from the group consisting of $Cl^-$, $HSO_4^-$, $HCO_3^-$, acetate, $SO_4^{2-}$ $CO_3^{2-}$, $PO_4^{3-}$ and $HPO_4^{2-}$, and provided that the co-catalyst is optional when the phase transfer catalyst comprises the $N^2$-alkyl-polyazapolycyclo-alkenium compound.

2. The method of claim 1, the method being characterizable by one or more of limitations (g), (h), (j), (k), (l), and (m):
   (g) step i) is performed under substantially anhydrous conditions by heating at a reaction temperature up to 180° C. for a reaction time up to 18 h;
   (h) the method further comprises step ii) removing at least a portion of a metal halide formed as a by-product in step i);
   (j) the method further comprises step iii) recovering an ester-functional silane formed in step i);
   (k) the method further comprises drying one or more of a), b), and c) before step i);
   (l) ingredient c) comprises a 8-octyl-1,8-diazabicyclo[5.4.0]-undec-7-enium bromide; a 8-2-ethylhexyl-1,8-diazabicyclo[5.4.0]-undec-7-enium bromide; a 8-octyl-1,8-diaza-bicyclo[5.4.0]-undec-7-enium chloride; a 7-2-ethylhexyl-7-methyl-1,5,7-triazabicyclo[4.4.0]dec-5-enium bromide; 5-butyl-7-methyl-1,5,7-triazabicyclo[4.4.0]dec-5-enium bromide; 5-octyl-7-methyl-1,5,7-triazaabicyclo[4.4.0]dec-5-enium bromide; 5-dodecyl-7-methyl-1,5,7-triazabicyclo[4.4.0]dec-5-enium bromide; 5-octyl-1,5-diazabicyclo[4.3.0]non-5-enium bromide, 5-nonyl-1,5-diazabicyclo[4.3.0]non-5-enium bromide, 5-decyl-1,5-diazabicyclo[4.3.0]non-5-enium bromide, 5-2-ethylhexyl-1,5-diazabicyclo[4.3.0]non-5-enium bromide, 5-didecyl-1,5-diazabicyclo[4.3.0]non-5-enium bromide or a combination thereof; and
   (m) the composition further comprises a metal acetate.

3. The method of claim 2, wherein the method is characterized by limitation (l).

4. The method of claim 1, where the composition further comprises an ingredient selected from the group consisting of e) a solvent, f) a stabilizer, and a combination thereof.

5. The method of claim 1, where the reaction temperature ranges from 60° C. to 180° C., and the reaction time is up to 12 hours.

6. The method of claim 1, where ingredient c) comprises an $N^2$-alkyl-polyazapolycyclo-alkenium compound.

7. The method of claim 6, wherein the $N^2$-alkyl-polyazapolycyclo-alkenium compound has a counter ion selected from the group consisting of $Cl^-$, $Br^-$, $HSO_4^-$, $HCO_3^-$, acetate, $SO_4^{2-}$, $CO_3^{2-}$ and $PO_4^{2-}$.

8. The method of claim 1, where ingredient c) comprises a bicyclic amidine.

9. The method of claim 8, where ingredient c) comprises 1,8-diazabicyclo[5.4.0]undec-7-ene; 1,5-diazabicyclo[4.3.0]non-5-ene; 7-methyl-1,5,7-triazabicyclo[4.4.0]dec-5-ene; or a combination thereof.

10. The method of claim 1, characterizable by limitation (n):
- (n) where ingredient a) has formula (I):

$$X_aSi(Q)_{(4-a)}, \text{ where} \quad (I)$$

subscript a is 1 or 2;
each X is independently a halogenated organic group; and
each Q is independently $R^1$ or $-OR^1$, wherein each $R^1$ is independently hydrocarbyl.

11. A method for producing a reaction product comprising an ester-functional silane, the method comprising: i) reacting a composition comprising:
- a) a haloorganosilane,
- b) a metal salt of a carboxy-functional compound,
- c) a phase transfer catalyst comprising a bicyclic amidine, an iminium compound, or a mixture thereof, and
- d) a co-catalyst, where the co-catalyst comprises a compound of formula: $M^{c+}R^{14}$, where $M^{c+}$ is alkali metal cation or alkaline earth metal cation, c is 1 or 2, and $R^{14}$ is a counter ion selected from the group consisting of $Cl^-$, $HSO_4^-$, $HCO_3^-$, acetate, $SO_4^{2-}$, $CO_3^{2-}$, $PO_4^3$ and $HPO_4^{2-}$.

* * * * *